US012673915B2

(12) United States Patent
Peng

(10) Patent No.: US 12,673,915 B2
(45) Date of Patent: Jul. 7, 2026

(54) PRECURSOR COMPOUND OF HEXAHYDRO-BETA-ACID COMPONENT COMPOUND, FEED COMPOSITION AND USE THEREOF

(71) Applicant: WISORIG TECHNOLOGIES PTE. LIMITED, Singapore (SG)

(72) Inventor: Xianfeng Peng, Guangzhou (CN)

(73) Assignee: WISORIG TECHNOLOGIES PTE. LIMITED, Singapore (SG)

( * ) Notice: Subject to any disclaimer, the term of this patent is extended or adjusted under 35 U.S.C. 154(b) by 498 days.

(21) Appl. No.: 18/036,908

(22) PCT Filed: Sep. 26, 2021

(86) PCT No.: PCT/CN2021/120638
§ 371 (c)(1),
(2) Date: May 15, 2023

(87) PCT Pub. No.: WO2022/022752
PCT Pub. Date: Feb. 3, 2022

(65) Prior Publication Data

US 2025/0346552 A1 Nov. 13, 2025

(30) Foreign Application Priority Data

Nov. 20, 2020 (CN) ........................ 202011314243.4

(51) Int. Cl.
*C07C 69/757* (2006.01)
*A23K 20/105* (2016.01)
*A61K 31/215* (2006.01)
*A61P 3/00* (2006.01)

(52) U.S. Cl.
CPC .......... *C07C 69/757* (2013.01); *A23K 20/105* (2016.05); *A61K 31/215* (2013.01); *A61P 3/00* (2018.01); *C07C 2601/16* (2017.05)

(58) Field of Classification Search
CPC .................................................... C07C 69/757
See application file for complete search history.

(56) References Cited

U.S. PATENT DOCUMENTS

| | | | | |
|---|---|---|---|---|
| 9,573,879 | B2 | 2/2017 | Peng et al. | |
| 12,133,541 | B2 * | 11/2024 | Peng .................... | A23K 20/111 |
| 2007/0280982 | A1 | 12/2007 | Ono et al. | |
| 2014/0363515 | A1 | 12/2014 | Funda et al. | |

FOREIGN PATENT DOCUMENTS

| | | | |
|---|---|---|---|
| CN | 106074471 | | 11/2016 |
| WO | 9852899 | A1 | 11/1998 |
| WO | 2016131204 | A | 8/2016 |

OTHER PUBLICATIONS

Nutter et al. CAS: 127: 257641.*
International Search Report of PCT/CN2021/120638, dated Dec. 7, 2021.
English Translation of International Search Report of PCT/CN2021/120638.
English Translation of WO2016131204.
English Translation of WO9852899A1.
English Translation of CN106074471.

* cited by examiner

*Primary Examiner* — Rei Tsang Shiao
(74) *Attorney, Agent, or Firm* — Kam Wah Law

(57) ABSTRACT

The present invention discloses the prodrugs of hexahydro-β-acid compounds, feed composition and use thereof, and a prodrug of hexahydro-β-acid compound of formula (I), or solvates thereof, or feed-acceptable salts thereof, wherein $R_1$ is selected from a substituted or unsubstituted $C_1$-$C_2$ alkyl, and each of $R_2$ and $R_3$ is independently selected from H and a linear or branched $C_2$-$C_4$ carbonyl, wherein the $C_2$-$C_4$ carbonyl is substituted or unsubstituted. Disclosed herein is that the prodrug of a hexahydro-β-acid compound from esterification by aliphatic acid exhibits excellent stability at high temperature to overcome the problem resulting from the degradation of hexahydro-β-acid compound in a high-temperature pelleting process. Furthermore, disclosed herein is that, both propionate and butyrate, the prodrugs of a hexahydro-β-acid compound from esterification by aliphatic acid, and feed-acceptable salt thereof and solvate thereof, are stable in high-temperature feed processing and achieve effects substantially equal to the hexahydro-β-acid compound in farm breeding.

(I)

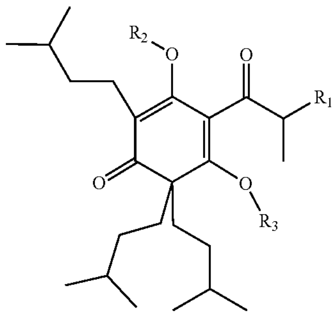

20 Claims, No Drawings

PRECURSOR COMPOUND OF HEXAHYDRO-BETA-ACID COMPONENT COMPOUND, FEED COMPOSITION AND USE THEREOF

CROSS REFERENCE TO RELATED APPLICATION

This is a U.S. national stage application of the International Patent Application No. PCT/CN2021/120638, filed Sep. 26, 2021, which is incorporated herein by reference in its entirety.

TECHNICAL FIELDS

The present invention relates to the field of an additive for animal feed, and particularly relates to a prodrug of a hexahydro-β-acid compound, feed composition thereof, and use thereof.

BACKGROUND

Hop plant produces organic acids known as hop acids, which include β-acids and β-acids, and have been used to replacing antibiotic in animal feed for the biological performance of sterilization, antibacterial activity or regulating metabolites. Among hop acids, β-acids have stronger antibacterial activity. Due to the poor stability and solubility, hop acids were usually mixed to an animal feed after grinding, or were sprayed and wrapped or mixed in/into an animal feed as a 1% aqueous solution of their potassium salts. The aforementioned usages for hop acids were inconvenient in animal breeding. It has been proposed that the derivatives of dihydrogenated, tetrahydrogenated, or hexahydrogenated hop acids exhibited changes in activity, stability, solubility, or other properties. However, unfortunately, it was soon known that hexahydrogenated β-acids and metallic salts thereof (referred to as hexahydro-β-acids) were unstable to heat. In addition, stored at room temperature, hexahydro-β-acids, mixed in a feed were degraded rapidly resulting in a decrease of hexahydro-β-acid content in feed. The rapid degradation of hexahydro-β-acids in a feed at room temperature could not satisfy the requirements of feed additive. The inventors have discovered that, the main components of hexahydro-β-acids are hexahydro-lupulone, hexahydro-colupulone and hexahydro-adlupulone, wherein the cause of instability of hexahydro-β-acids in feed at room temperature is due to the instability of hexahydro-lupulone resulting in the decrease of the content of hexahydro-β-acids. The inventors have further discovered that, hexahydro-colupulone or the combination of hexahydro-colupulone and hexahydro-adlupulone in premixes achieved similar or even better effect on the production performance of an animal as or than hexahydro-β-acids. However, the decrease of the content of hexahydro-colupulone and/or hexahydro-adlupulone in feed at storage limits their use in breeding industry.

In view of the above, the present invention is proposed.

SUMMARY

The objects provided herein comprise providing a prodrug of a hexahydro-β-acid compound.

The objects provided herein also comprise providing feed composition comprising the prodrug of a hexahydro-β-acid compound.

The objects provided herein also comprise providing the use of the prodrug of hexahydro-β-acid compound or the feed composition thereof in the preparation of a additive for animal feed.

The objects provided herein also comprise providing the use of the prodrug of a hexahydro-β-acid compound or the feed compositions thereof in the preparation of an animal feed.

The objects provided herein also comprise providing a method for improving the production performance of an animal.

To achieve at least one of the objects provided herein, the following technical solutions are proposed.

In one aspect, provided herein is a prodrug of a hexahydro-β-acid compound of formula (I), or a solvate thereof, or a feed-acceptable salt thereof, Wherein, $R_1$ is a linear or branched alkyl group, wherein the alkyl group is substituted or unsubstituted; each of $R_2$ and $R_3$ is independently selected from H and a linear or branched aliphatic carbonyl, wherein the carbonyl is substituted or unsubstituted.

(I)

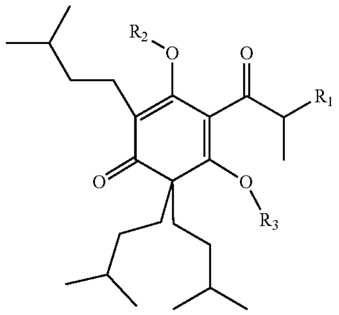

In another aspect, provided herein is a feed composition, wherein the feed composition comprises an optional feed-acceptable adjuvant, and a prodrug of formula (I) or a solvate thereof or a feed-acceptable salt thereof.

In another aspect, provided herein is the use of a prodrug of formula (I), a solvate thereof, a feed-acceptable salt thereof and a feed composition in the preparation of additives for animal feed, wherein the feed composition comprises a prodrug of formula (I) or a solvate thereof or a feed-acceptable salt thereof.

In another aspect, provided herein is the use of a prodrug of formula (I), a solvate thereof, a feed-acceptable salt thereof, and a feed composition in the preparation of an animal feed, wherein the feed composition comprises a prodrug of formula (I) or a solvate thereof or a feed-acceptable salt thereof.

In another aspect, provided herein is a method for improving the production performance of an animal, comprising:

- feeding an animal with the prodrug provided herein or a solvate thereof or a feed-acceptable salt thereof, or,
- feeding an animal with the feed composition provided herein, or,
- feeding an animal with a feed comprising the feed composition provided herein.

Compared with prior art, the technical effects provided herein are:

Discovered herein is that the prodrug of a hexahydro-β-acid compound from esterification by aliphatic acid, exhibit excellent stability at high temperature, to overcome the problem resulting from the degradation of hexahydro-β-acid compound in a high-temperature pelleting process. Furthermore, discovered herein is that, both propionate and butyrate, the prodrugs of a hexahydro-β-acid compound from esterification by aliphatic acid, and feed-acceptable salt thereof and solvate thereof, are stable in high-temperature feed processing and achieve effects substantially equal to the hexahydro-β-acid compound in farm breeding.

Any embodiment of any aspect provided herein can be combined with other embodiments as long as there is no contradiction between them.

DETAILED DESCRIPTION OF THE EMBODIMENTS

The foregoing described herein merely outlines certain aspects provided herein, but is not limited to these aspects. The above aspects and other aspects will be described in more detail and completely as below.

DETAILED DESCRIPTION OF THE INVENTION

Certain embodiments provided herein will be described in detail, examples of which are illustrated by the accompanying structures and formulas. The disclosure intends to encompass all alternatives, modifications and equivalents, which are all within the scope of the disclosure as defined by the appended claims. In addition, certain technical features disclosed herein, which are, for clarity, described separately in multiple independent embodiments, can also be provided in combination in an individual embodiment or in any suitable sub-combination.

Compound

A compound involved herein is a prodrug of a hexahydro-β-acid compound of formula (I).

(I)

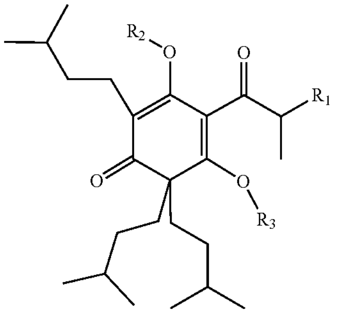

$R_1$ is a linear or branched alkyl, wherein the alkyl is substituted or unsubstituted; each of $R_2$ and $R_3$ is independently selected from H and a linear or branched aliphatic carbonyl, wherein the aliphatic carbonyl is substituted or unsubstituted.

Further, $R_1$ is selected from a substituted or unsubstituted $C_1$-$C_2$ alkyl; each of $R_2$ and $R_3$ is independently selected from H and a linear or branched $C_3$-$C_4$ carbonyl, wherein the $C_3$-$C_4$ carbonyl is substituted or unsubstituted.

The "hexahydro-β-acid compound" involved herein refers to the main component of hexahydro-β-acids, i.e., hexahydro-colupulone (I1-1), hexahydro-adlupulone (I1-2), and hexahydro-lupulone (I1-3), wherein the formulas thereof are as follows:

(I1-1)

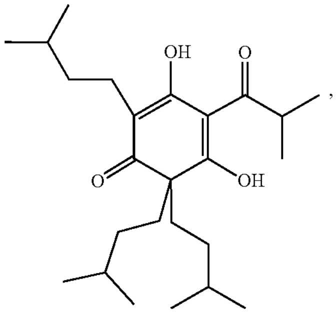

, (I1-2)

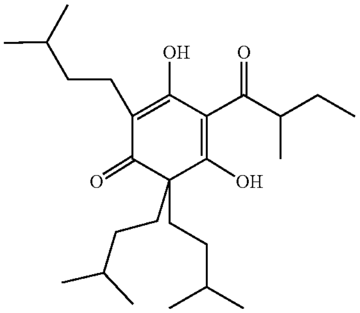

, and (I1-3)

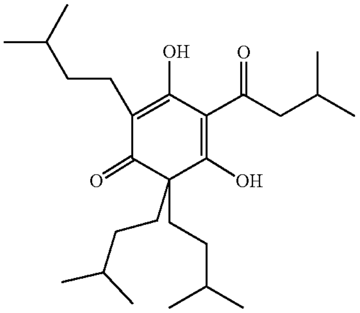

.

Generally, the term "substituted" indicates that one or more replaceable hydrogen atoms in the given formula have been substituted by specific group, wherein one substituted group may be substituted by a group at each substitutable position thereof, and when there are more than one position to be substituted by one or more specific groups in the given formula, then the groups thereof can be identical or different.

The term "$C_a$-$C_b$ alkyl" provided herein is a linear or branched saturated alkyl group of a to b carbon atoms, such as methyl, ethyl, propyl, isopropyl, . . . ; for example, the term "$C_3$-$C_4$ alkyl" represents a linear or branched saturated alkyl group of 3 to 4 carbon atoms. The term "$C_a$-$C_b$ carbonyl" is a linear or branched aliphatic carbonyl group of a to b carbon atoms, such as $C(=O)CH_2CH_3$, $C(=O)(CH_2)_2CH_3$, $C(=O)CH_2(CH_3)_2$, and so on.

In some embodiments, in the prodrug of formula (I), $R_1$ is $CH_3$, and each of $R_2$ and $R_3$ is independently selected from H and a linear or branched $C_3$-$C_4$ carbonyl, wherein the $C_3$-$C_4$ carbonyl are substituted or unsubstituted.

Further, the $R_2$ and $R_3$ are each independently selected from H and unsubstituted linear $C_3$-$C_4$ carbonyl, and preferably not both H.

In some examples, $R_3$ is H, and $R_2$ is an unsubstituted linear $C_3$-$C_4$ carbonyl.

In some other examples, $R_2$ and $R_3$ are each independently selected from the unsubstituted linear $C_3$-$C_4$ carbonyl, and preferably the same.

In some embodiments, in the prodrug of formula (I), $R_1$ is $CH_2CH_3$, and each of $R_2$ and $R_3$ is independently selected from H and linear or branched $C_3$-$C_4$ carbonyl, wherein the $C_3$-$C_4$ carbonyl are substituted or unsubstituted.

Further, the $R_2$ and $R_3$ are each independently selected from H and unsubstituted linear $C_3$-$C_4$ carbonyl, and preferably not both H.

In some examples, $R_3$ is H, and $R_2$ is an unsubstituted linear $C_3$-$C_4$ carbonyl.

In some other examples, $R_2$ and $R_3$ are each independently selected from unsubstituted linear $C_3$-$C_4$ carbonyl, and preferably the same.

In some other specific examples, the prodrugs of a hexahydro-β-acid compound described herein include:

(I2-1)

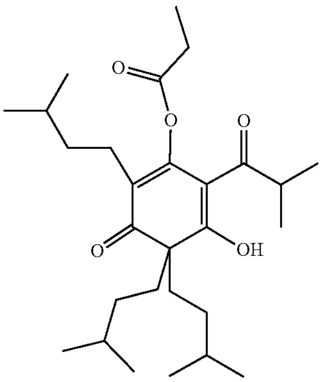

, (I2-2)

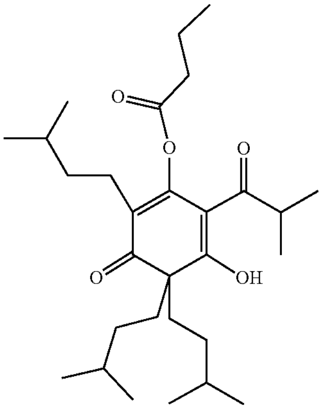

, (I2-3)

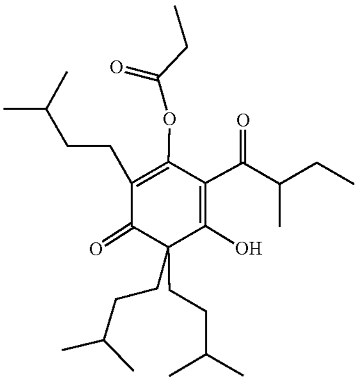

,

-continued (I2-4)

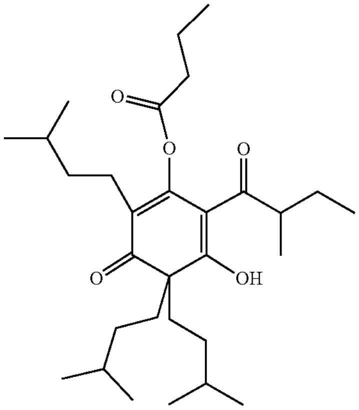

, (I2-5)

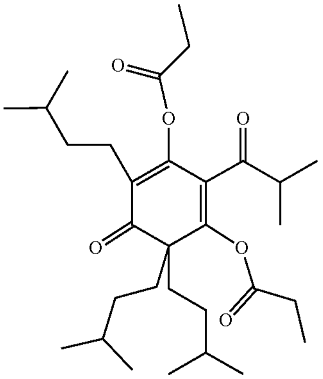

, (I2-6)

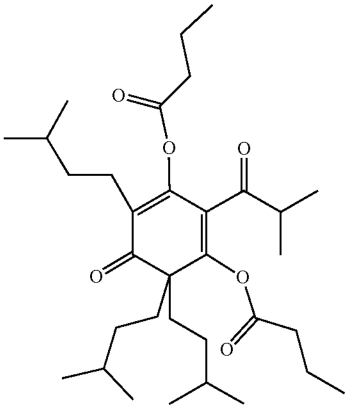

, (I2-7)

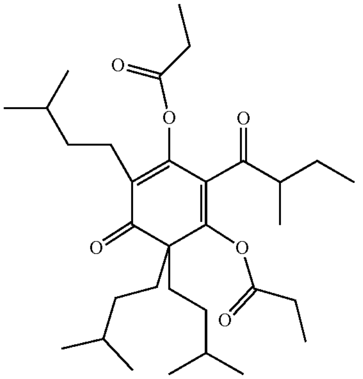

, and

-continued (I2-8)

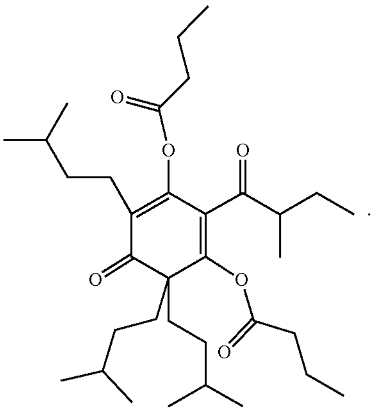

Preparation and Purification of the Compound

The prodrug of a hexahydro-β-acid compound involved herein can be prepared using the procedure below.

(1) The commercially available hop extract as raw material. is extracted with organic solvents to give β-acids.

(2) The β-acids are hydrogenated to give hexahydro-β-acids.

(3) The hexahydro-β-acids are subjecting to recrystallization or preparative chromatography to give hexahydro-β-acid compounds, wherein the compounds are knowns as hexahydro-colupulone (I1-1), hexahydro-adlupulone (I1-2), and hexahydro-lupulone (I1-3).

(4) The hexahydro-β-acid compound is esterified with one stoichiometric or two stoichiometrics linear or branched fatty acid to give the prodrug of the hexahydro-β-acid compound, wherein the fatty acid is substituted or unsubstituted.

The hexahydro-β-acid compound with asymmetric centers is a mesomer, a racemate, a stereoisomer, a geometric isomer, a tautomer, a single enantiomer, a single diastereomer, or a combination thereof. It should be noted that prodrugs of the isomer forms via the above-mentioned step (4) are included herein. The hexahydro-β-acid compound can be provided commercially, or prepared by semi-synthesis with plant-sourced raw materials or total-synthesis by skilled chemists.

In some embodiments, the preparation procedure of the prodrug of a hexahydro-β-acid compound provided herein also involves the workup steps known as isolation, purification, or recrystallization of the product. The product can be obtained as a crude product from the reaction system by removing the solvent. In order to obtain a solid substance with higher chemical purity and lower impurity content, the crude products are dissolved, crystallized or precipitated or recrystallized and separated in alcohol solvent, alcohol-water mixed solvent or other organic solvents that can be used for product recrystallization under suitable temperature, light and mechanical vibration conditions, to give a prodrug of a hexahydro-β-acid compound in a certain crystal form. The prodrug of a hexahydro-β-acid compound in a certain crystal form refers to the said prodrug or a solvate thereof. The solvate thereof can be selected from a hydrate of the prodrug and the prodrug with ethanol.

The term "solvate" involved herein refers to a co-crystal associate formed by contacting the compound provided herein with a stoichiometric or non-stoichiometric solvent via non-covalent intermolecular forces due to external conditions and internal conditions. Solvents that form solvate include, but are not limited to water, acetone, ethanol, methanol, dimethyl sulfoxide, ethyl acetate, acetic acid, isopropanol, and the like. The term "hydrate" refers to a complex or a crystal with water, i.e., a compound with stoichiometric or non-stoichiometric water molecules via non-covalent intermolecular forces.

In order to obtain a purer solid substance with impurity in lower content, the preparation procedure of the prodrug provided herein may also involve a salting-out step. The salting-out step gives a feed-acceptable salt of a prodrug of a hexahydro-β-acid compound with the corresponding organic base, inorganic base, organic acid or inorganic acid under the principle of acid-base neutralization, acid-base coordination, or acid-base chelation to precipitate. Wherein the inorganic acid includes, but is not limited to, hydrochloric acid, hydrobromic acid, phosphoric acid, sulfuric acid, nitric acid, or a combination thereof. Wherein the organic base includes, but is not limited to, ammonia or triethylamine. Wherein the inorganic base includes, but is not limited to, sodium hydroxide, potassium hydroxide, magnesium hydroxide, or calcium hydroxide.

The feed-acceptable salt refers to a salt formed by the prodrug of a hexahydro-β-acid compound provided herein and an organic base, inorganic base, organic acid or inorganic acid, wherein the bases or the acids are non-toxic to animals. The term "feed-acceptable" refers to a substance or composition which should be chemically or toxicologically suitable for and relevant to the resulting feed or the farm animal.

In some embodiments, the workup step of the prodrug of a hexahydro-β-acid compound provided herein also involves a salting-out process to form an acid-base salt and/or acid-base chelate salt with an inorganic acid or organic acid. Wherein the organic acid includes, but is not limited to, acetic acid, maleic acid, succinic acid, mandelic acid, fumaric acid, malonic acid, malic acid, 2-hydroxypropionic acid, pyruvic acid, oxalic acid, glycolic acid, salicylic acid, glucuronic acid, galactonic acid, citric acid, tartaric acid, aspartic acid, glutamic acid, benzoic acid, p-toluic acid, cinnamic acid, p-toluenesulfonic acid, benzenesulfonic acid, methanesulfonic acid, ethanesulfonic acid, trifluoromethanesulfonic acid, or a combination thereof.

Use of the Compound

The prodrug of a hexahydro-β-acid compound provided herein, the solvate thereof, or the feed-acceptable salt thereof, can be used in the preparation of an additive for animal feed.

The "animal" involved herein refers to a human or a farmed animal that is unable to convert inorganics into organics, and can only use organics as food for life activities such as ingestion, digestion, absorption, respiration, circulation, excretion, sensation, movement, and reproduction. The "farm animals" include poultry, livestock, aquatic animals, and other animals that are legally captured in captivity, including pets, such as cats and dogs. The term "livestock" refers to, for example, any one of pigs, cattle, horses, goats, sheep, deer, and any species of a variety of useful rodents. The term "poultry" includes, for example, chickens, ducks, geese, quails, pigeons, and the like. The term "aquatic animal" includes, for example, fish, shrimp, turtle, soft-shelled turtle, and the like.

The use of the prodrug of a hexahydro-β-acid compound provided herein, the solvate thereof, or the feed-acceptable salt thereof, is in the preparation of a non-nutritive feed additive for improving the production performance of an animal at every growth stage, wherein the animal can be selected from livestock, poultry, an aquaculture animal or a pet animal at various growth stages.

In further embodiments, the livestock includes but is not limited to pigs, cattle, sheep, horses, rabbits, martens and donkeys; the poultry includes but is not limited to chickens, turkeys, ducks, geese, quails or pigeons; the aquaculture animals include but are not limited to fish, shrimps, turtles, crabs, soft-shelled turtles, bullfrogs, eels and loaches; the pet animals include but are not limited to dogs or cats of various subspecies.

In one embodiment, the use of the prodrug of a hexahydro-β-acid compound provided herein, the solvate thereof, or the feed-acceptable salt thereof, is in the preparation of an additive for feed for improving the production performance of a hog, possessing improvement effect on the feed intake, average daily weight gain and feed efficiency.

In another embodiment, the additive for a feed, prepared from the prodrug of a hexahydro-β-acid compound provided herein, the solvate thereof, or the feed-acceptable salt thereof, can significantly improve the production performance of a broiler or a layer.

In another embodiment, the use of the prodrug of a hexahydro-β-acid compound provided herein, the solvate thereof, or the feed-acceptable salt thereof, is used in preparation of an additive for a feed, wherein the feed can improve the production performance of fish.

Feed Compositions of the Invention

Provided herein is a stable feed composition comprising the prodrug of formula (I), a solvate thereof, or a feed-acceptable salts thereof, and an optional feed-acceptable adjuvant, wherein the feed-acceptable adjuvant is a carrier, a diluent, a excipient and a dissolvent, or a combination thereof.

The "composition" as used herein refers to a set of compounds comprising one or more compounds as active ingredients.

The terms "comprise," "included", "including", "include", "comprising," "with" and variants thereof, as used herein, are an open expression, which not only includes those specified herein, but does not exclude other aspects. However, it should be noted that the feed composition provided herein excludes hexahydro-lupulone or a salt or ester thereof. In one or more embodiments, except for the prodrug of formula (I), the feed composition provided herein does not comprise other hexahydro-β-acid compounds or the salts and esters thereof (except for the other a hexahydro-β-acid compound in an amount as an unavoidable impurity).

The "stable feed composition" as used herein refers to a composition for animal consumption, which is stable enough to be prepared, and in which the integrity of compounds can be kept for a long enough period of time for the purpose described in detail herein.

The "carrier" as used herein refers to a feedable substance, that exhibits favorable chemical stability and absorbable property and capable of carrying active ingredients, wherein the dispersibility of the ingredient is improved. The carriers is an organic or inorganic carrier. Organic carrier is material rich in crude fibers, including but not limited to corn flour, corn cob flour, wheat bran, rice husk flour, defatted rice bran, rice mill by-product, corn stalk flour, peanut husk flour, and the like. Inorganic carrier is mineral, which is mainly classified into calcium salts and silicon oxides, and is used for the preparation of a trace element premix, including but not limited to calcium carbonate, silicate, vermiculite, zeolite, sepiolite, and the like.

The "diluent" as used herein refers to a substance that distributes the starting additive evenly in the, and dilutes the high-concentration starting additive into low-concentration premix, which separates trace components from each other and reduces interactions between or among active ingredients to increase the stability of the active ingredients without affecting the physicochemical properties of involved substances. The diluent is an organic diluent or inorganic diluent. Organic diluents include, but are not limited to, corn flour, degeminated corn flour, dextrose (glucose), sucrose, semolina with bran, fried soybean flour, secondary flour, corn gluten meal, and the like. Inorganic diluents include, but are not limited to, limestone, calcium dihydrogen phosphate, shell powder, kaolin (white clay), sodium chloride and sodium sulfate.

The excipient is selected from the group consisting of wetting agent, adhesive, disintegrant, anti-adhesion agent, and the combination thereof. Wherein, the wetting agent is an agent that can induce the inherent viscosity of a substance, adhesive is an agent that can bind other agents together, disintegrant is an agent that breaks the entire sheet of a substance into many small particles, retention aid is an agent that reduces the friction between particles, and anti-adhesion agent is an agent that prevent material adhesion, including but not limited to magnesium stearate, talc, vegetable oil, magnesium lauryl sulfate, starch, starch slurry, water, inorganic salts, dextrin, powdered sugar, and the like.

The "dissolvent" as used herein refers to a solvent required to dissolve or disperse solids, including but not limited to water, glycerin, ethanol, and the like.

In some embodiments, the prodrug included in the feed composition is a prodrug of hexahydro-colupulone, or a solvate thereof, or a feed-acceptable salt thereof.

In one embodiment, the prodrug included in the feed composition is a hexahydro-colupulone mono-propionate of formula (I2-1), or a solvate thereof, or a feed-acceptable salt thereof.

In one embodiment, the prodrug included in the feed composition is a hexahydro-colupulone mono-butyrate of formula (I2-2), or a solvate thereof, or a feed-acceptable salt thereof.

In one embodiment, the prodrug included in the feed composition is a hexahydro-colupulone di-propionate of formula (I2-5), or a solvate thereof, or a feed-acceptable salt thereof.

In one embodiment, the prodrug included in the feed composition is a hexahydro-colupulone di-butyrate of formula (I2-6), or a solvate thereof, or a feed-acceptable salt thereof.

In some embodiments, the prodrug included in the feed composition is a prodrug of hexahydro-adlupulone, or a solvate thereof, or a feed-acceptable salt thereof.

In one embodiment, the prodrug included in the feed composition is a hexahydro-adlupulone mono-propionate of formula (I2-3), or a solvate thereof, or a feed-acceptable salt thereof.

In one embodiment, the prodrug included in the feed composition is a hexahydro-adlupulone mono-butyrate of formula (I2-4), or a solvate thereof, or a feed-acceptable salt thereof.

In one embodiment, the prodrug included in the feed composition is a hexahydro-adlupulone di-propionate of formula (I2-7), or a solvate thereof, or a feed-acceptable salt thereof.

In one embodiment, the prodrug included in the feed composition is a hexahydro-adlupulone di-butyrate of formula (I2-8), or a solvate thereof, or a feed-acceptable salt thereof.

In some embodiments, the prodrug included in the feed composition is a combination of a hexahydro-colupulone, a solvate thereof, or a feed-acceptable salt thereof, and a prodrug of hexahydro-adlupulone, a solvate thereof, or a feed-acceptable salt thereof.

Specifically, the combination of a prodrug of hexahydro-colupulone and a prodrug of hexahydro-adlupulone, includes but is not limited to a combination of hexahydro-colupulone mono-propionate and hexahydro-adlupulone mono-propionate, a combination of hexahydro-colupulone mono-butyrate and hexahydro-adlupulone mono-butyrate, a combination of hexahydro-colupulone di-propionate and hexahydro-adlupulone mono- or di-ester, and a combination of hexahydro-colupulone di-butyrate and hexahydro-adlupulone di-butyrate.

In some embodiments, the prodrug included in the feed composition is a combination of a prodrug of hexahydro-colupulone, a solvate thereof, or a feed-acceptable salt thereof, and a prodrug of hexahydro-adlupulone, a solvate thereof, or a feed-acceptable salt thereof, wherein, the weight of the prodrug of hexahydro-colupulone is deemed to be 1 unit and the weight of the prodrug of hexahydro-adlupulone is not more than 0.5 unit and not less than 0.01 unit.

In some embodiments, the prodrug included in the feed composition is a combination of a prodrug of hexahydro-colupulone, a solvate thereof, or a feed-acceptable salt thereof, and a prodrug of hexahydro-adlupulone, a solvate thereof, or a feed-acceptable salt thereof, wherein the weight of the prodrug of hexahydro-colupulone is deemed to be 1 unit, and the weight of the prodrug of hexahydro-adlupulone is 0.5 unit.

In some embodiments, the prodrug included in the feed composition is a combination of a prodrug of hexahydro-colupulone, a solvate thereof, or a feed-acceptable salt thereof, and a prodrug of hexahydro-adlupulone, a solvate thereof, or a feed-acceptable salt thereof, wherein the weight of the prodrug of hexahydro-colupulone is deemed to be 1 unit, the weight of the prodrug of hexahydro-adlupulone is 0.25 unit.

In some embodiments, the aforementioned feed composition further comprises an additional feed additive for animals and/or animal feed ingredients.

The feed additive for animal is a nutritional additive, a general feed additive, or a medicinal feed additive.

Nutritional additive refers to a product, in a small or trace amount, that are added to a formula feed to meet the need for certain nutrients, or to improve feed utilization, and to achieve direct nutritional effects on animals, including but not limited to amino acids, amino acid salts and analogs thereof, vitamins and vitamin-like substances, trace elements and their complexes (chelates), microbial enzyme preparations, or non-protein nitrogen.

General feed additive, also known as non-Nutritional additive, refers to a non-Nutritional product added into the feed to improve feed utilization, to achieve an effect on the feed quality and properties and to achieve a good effect on animal health or metabolism, and includes but is not limited to a growth enhancer, an insect repellent, a flavor, an attractant, a regulator, a preparation for feed, a preservative and an antioxidant for feed, and a Chinese herbal medicine additive.

In some embodiments, the additional feed additive included in the feed composition is selected from the group consisting of a nutritional additive, a non-nutritional additive, a medicinal feed additive, and the combinations thereof.

Further specifically, the non-nutritional additive is a growth enhancer, including but not limited to butyric acid, calcium butyrate, sodium butyrate, tannic acid, p-thymol, p-thymol ester, p-thymol salt, 2-hydroxybenzoic acid, benzoic acid or calcium benzoate, zinc oxide, zinc sulfate, and zinc chloride.

In one embodiment, the non-nutritional additive is calcium butyrate.

In another embodiment, the non-nutritional additive is tannic acid.

Further specifically, the medicinal feed additive includes but is not limited to a premix of a veterinary drug with carrier or diluent, and is used in a feed for long-term to prevent an animal disease and to achieve a good effect on animal growth.

Further specifically, the medicinal feed additive is an antibiotic for feed, including but not limited to polymyxin, salinomycin, avilamycin, bacitracin, virginiamycin, nasitide, flavomycin, enramycin, kitasamycin, olaquindox, oxytetracycline, or chlortetracycline.

In some embodiments, the animal feed ingredients are grains, oilseeds, legumes, tubers/tuberous roots, other seeds, forages/roughages, other plants/algae, and processed products thereof, are also dairy products, products of terrestrial animal, products of fish and other aquatic organisms and by-products thereof, are also trace elements, microbial fermentation products and by-products thereof, and other feed ingredients.

Use of the Feed Compositions

Provided herein is the use of a stable feed composition afore-mentioned, wherein the feed composition comprises an optional feed-acceptable adjuvant, and a prodrug of a hexahydro-β-acid compound of formula (I), solvates thereof, and feed-acceptable salts thereof.

In some embodiments, the afore-mentioned stable feed composition is used in the preparation of feed additives for animals, wherein the feed composition comprises an optional feed-acceptable adjuvant, and a prodrug of a hexahydro-β-acid compound of formula (I), solvates thereof, and feed-acceptable salts thereof.

Furthermore, the feed additives for animal are additives used to increase the production performance of animals, and include but are not limited to feed additives for livestock, poultry, aquatic animal and pet.

Specifically, the afore-mentioned stable feed composition is used in the preparation of feed additives for livestock including but not limited to pigs, cattle, sheep, horses, rabbits, minks, and the like of various growth stages, wherein the feed composition comprises an optional feed-acceptable adjuvant, and a prodrug of a hexahydro-β-acid compound of formula (I), solvates thereof, and feed-acceptable salts thereof.

Specifically, the afore-mentioned stable feed composition is used in the preparation of feed additives for poultry including but not limited to chickens, ducks, geese, pigeons, and the like of various growth stages, wherein the feed composition comprises an optional feed-acceptable adjuvant, and a prodrug of a hexahydro-β-acid compound of formula (I), solvates thereof, and feed-acceptable salts thereof.

Specifically, the afore-mentioned stable feed composition is used in the preparation of feed additives for aquatic animals including but not limited to fish, shrimps, crabs, soft-shelled turtles, eels, and the like of various growth stages, wherein the feed composition comprises an optional feed-acceptable adjuvant, and a prodrug of a hexahydro-β-acid compound of formula (I), solvates thereof, and feed-acceptable salts thereof.

Specifically, the afore-mentioned stable feed composition is used in the preparation of feed additives for pets including but not limited to Artificially bred dogs or cats, wherein the feed composition comprises an optional feed-acceptable adjuvant, and a prodrug of a hexahydro-β-acid compound of formula (I), solvates thereof, and feed-acceptable salts thereof.

In some embodiments, the animal feed additives, prepared from the afore-mentioned stable feed composition, are premixes, multi-premixes, aqueous solutions, or granules, wherein the feed composition comprises an optional feed-acceptable adjuvant, and a prodrug of a hexahydro-β-acid compound of formula (I), solvates thereof, and feed-acceptable salts thereof.

In some embodiments, the afore-mentioned stable feed composition, is used in the preparation of animal feeds, wherein the feed composition comprises an optional feed-acceptable adjuvant, and a prodrug of a hexahydro-β-acid compound of formula (I), solvates thereof, and feed-acceptable salts thereof.

The feed provided herein refer to a product that is processed and produced by industrialization for animal consumption.

The animal feeds, prepared from the afore-mentioned stable feed composition comprising an optional feed-acceptable adjuvant, and a prodrug of a hexahydro-β-acid compound of formula (I), solvates thereof, and feed-acceptable salts thereof, are feeds for livestock, poultry, aquatic animal, pet, and the like.

Specifically, the afore-mentioned stable feed composition is used in the preparation of feeds for livestock, wherein the feed composition comprises an optional feed-acceptable adjuvant, and a prodrug of a hexahydro-β-acid compound of formula (I), solvates thereof, and feed-acceptable salts thereof, and the livestock includes but is not limited to pigs, cattle, sheep, horses, rabbits, minks, and the like of various growth stages.

Specifically, the afore-mentioned stable feed composition is used in the preparation of feeds for poultry, wherein the poultry includes but is not limited to chickens, ducks, geese, pigeons, and the like of various growth stages, and the feed composition comprises an optional feed-acceptable adjuvant, and a prodrug of a hexahydro-β-acid compound of formula (I), solvates thereof, and feed-acceptable salts thereof.

Specifically, the afore-mentioned stable feed composition is used in the preparation of feeds for aquatic animals, wherein the aquatic animals include but are not limited to fish, shrimps, crabs, soft-shelled turtles, eels, and the like of various growth stages, and the feed composition comprises an optional feed-acceptable adjuvant, and a prodrug of a hexahydro-β-acid compound of formula (I), solvates thereof, and feed-acceptable salts thereof.

Specifically, the afore-mentioned stable feed composition is used in the preparation of feeds for pets, wherein the pets include but are not limited to farm-raised dogs or cats, and the feed composition comprises an optional feed-acceptable adjuvant, and a prodrug of a hexahydro-β-acid compound of formula (I), solvates thereof, and feed-acceptable salts thereof.

In some embodiments, the animal feeds prepared from the above-mentioned stable feed composition are single feeds, concentrated feeds, formula feeds, multi-premixes, or concentrate supplements, wherein the feed composition comprises an optional feed-acceptable adjuvant, and a prodrug of a hexahydro-β-acid compound of formula (I), solvates thereof, and feed-acceptable salts thereof.

Specifically, the formula feeds are complete formula feeds.

Methods for Improving Production Performance of Farmed Animals

In some feeding embodiments, the afore-mentioned stable feed composition and the additive for feed prepared from the feed composition are administered to an animal along with a feed by a farmer to significantly increase the production performance of the animal, wherein the feed composition comprises an optional feed-acceptable adjuvant, and a prodrug of a hexahydro-β-acid compound of formula (I), solvates thereof, and feed-acceptable salts thereof.

Optionally, the feed composition is a premix of an additive for feed, a multi-premix of an additive for feed, a granule, or an aqueous solution, and is administered to an animal along with a feed.

In one embodiment, the feed composition is a premix of an additive for feed.

In one embodiment, the feed composition is a multi-premix of an additive for feed.

In some embodiments, the additive for feed is a premix, a multi-premix, a granule, or an aqueous solution, and is mixed with a feed for animal to feed animals.

The animals are livestock, poultry, aquatic animals, or pets.

Specifically, the livestock include but are not limited to pigs, cattle, sheep, horses, rabbits, minks, and the like at various growth stages; the poultry include but are not limited to chickens, ducks, geese, pigeons, and the like at various growth stages; the aquatic animals include but are not limited to fish, shrimps, crabs, soft-shelled turtles, eels, and the like at various growth stages; the pets include but are not limited to Artificially bred dogs or cats.

In one embodiment, an additive for feed is administered to a weaned pig along with a feed by a farmer to significantly increase the average daily weight gain and feed efficiency of the weaned pig, wherein the additive comprises a prodrug of a hexahydro-β-acid compound of formula (I), solvates thereof, and feed-acceptable salts thereof.

In one embodiment, the afore-mentioned stable feed composition and the additive for feed prepared from the feed composition are administered to a broiler along with a feed by a farmer to significantly reduce the feed conversion ratio to increase the feed efficiency of the broiler, wherein the feed composition comprises an optional feed-acceptable adjuvant, and a prodrug of a hexahydro-β-acid compound of formula (I), solvates thereof, and feed-acceptable salts thereof.

In one embodiment, the afore-mentioned stable feed composition and the additive for feed prepared from the feed composition are administered to fish along with a feed, wherein the feed composition comprises an optional feed-acceptable adjuvant, and a prodrug of a hexahydro-β-acid compound of formula (I), solvates thereof, and feed-acceptable salts thereof.

In one embodiment, the afore-mentioned stable feed composition and the additive for feed prepared from the feed composition are administered to a young dog along with a feed, wherein the feed composition comprises an optional feed-acceptable adjuvant, and a prodrug of a hexahydro-β-acid compound of formula (I), solvates thereof, and feed-acceptable salts thereof.

In some other feeding embodiments, a feed for an animal prepared from the afore-mentioned stable feed composition is administered to an animal along with a feed by a farmer to significantly increase the production performance of the animal, wherein the composition comprises an optional feed-acceptable adjuvant, and a prodrug of a hexahydro-β-acid compound of formula (I), solvates thereof, and feed-acceptable salts thereof.

Optionally, the feed composition is a concentrated feed, a formula feed, a multi-premix, or a concentrate supplement, and directly administered to an animal as a feed for animal.

The premix of an additive for a feed as used herein refers to a homogeneous mixture prepared by mixing a prodrug of a hexahydro-β-acid compound provided herein, an additive for feed other than the prodrug of a hexahydro-β-acid compound, a carrier and/or a diluent, a combination mainly comprising two or more than two kinds of nutritional additive for feed, and the like at a certain ratio, wherein the nutritional additive is a mineral trace element, a vitamin, a microorganism, an amino acid, and the like at a content sufficient to meet the need for the basic nutrients of an animal applied thereto at specific physiological stages, and is added into a formula feed, a concentrate supplement, or a drinking water for an animal, at a content of not less than 0.1% and not more than 10%.

The concentrated feed as used herein refers to a feed mainly prepared by mixing proteins, minerals, feed additives, and the like at a certain ratio.

Formula feed as used herein refers to a feed prepared by mixing multiple feed ingredients for animal, additives for feed, and the like at a certain ratio to meet the need for nutrients of a farmed animal.

The concentrate supplement as used herein refers to a feed prepared by mixing multiple feed ingredients for animal, additives for feed, and the like at a certain ratio to achieve an effect on supplement for nutrients of a herbivore.

In one embodiment, the feed composition is a complete formula feed.

The embodiments provided herein will be described in detail below with examples, but those skilled in the art will understand that the following examples are only used to illustrate the present invention and should not be regarded as a limiting to the scope of the present invention. In the examples, if specific conditions are not indicated, they shall be carried out in the conventional conditions or the conditions recommended by the manufacturer. Where the involved reagents or instruments are presented without manufactures' names, they are all conventional products and can be purchased commercially.

Example A: Semi-Synthesis of a Prodrug of a Hexahydro-β-Acid Compound

Those skilled in the art will recognize that other preparation methods of a hexahydro-β-acid compound provided herein are all considered to be within the disclosure as defined by the appended claims. For example, the non-exemplified synthesis of the hexahydro-β-acid compounds provided herein can be carried out by the skilled personnel in the art with modified methods, such as the methods including appropriate protection of other groups, the use of other reagents, regular modifications of the reaction conditions, and the like.

A1: Preparation of β-Acids

To a 5 L beaker were sequentially added 1 kg of hop extract, 3 L of pure water, and 1 L of ethanol, with stirring to dissolve the hop extract. To the reaction mixture was added 0.5 L of KOH solution dropwise to give pH 13, left for a while and then filtered to remove insoluble substances. To the filtrate was pumped $CO_2$ gas to give pH 8.5, cooled and left for 2 hours, and then filtered to collect the crude product.

The above crude product was dissolved in 200 mL of n-hexane, and the resulting organic solution was washed with water (150 mL×3) and then concentrated to give a paste. The paste was then dissolved in 300 mL of KOH solution at pH 12.5. The resulting mixture was washed with n-hexane (200 mL×3), and the organic phase was abandoned. To the resulting water phase was added an acid to give pH8.5 and extracted by n-hexane (200 mL×3). The combined organic phase was dried over anhydrous sodium sulfate, and concentrated by vacuum evaporation to give 400 g of 3-acid crystal. The result HPLC analysis illustrated that the 3-acid crystal mainly contained colupulone, adlupulone, and lupulone.

A2: Preparation of Hexahydro-β-Acids 50 g of the 3-acid crystal was dissolved in 300 mL of 95% ethanol solution, followed by the addition of 1.7 g of 10% Pd/C. The mixture was stirred under hydrogen atmosphere at room temperature overnight. The reaction was monitored to endpoint by HPLC. The reaction solution was filtered and the filtrate was concentrated to give 46 g of hexahydro-β-acids as a crystal.

A3: Separation and Purification of the Main Components of Hexahydro-β-Acids

A3.1 Preparation of Hexahydro-Colupulone

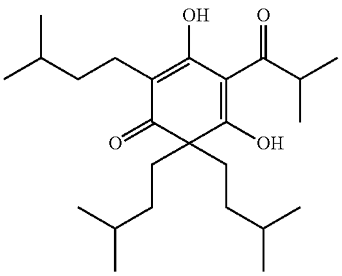 [SMILES: CC(C)CCC1=C(O)C(C(=O)C(C)C)=C(O)C(CCC(C)C)(CCC(C)C)C1=O]

Hexahydro-β-acids was recrystallized in n-hexane to give hexahydro-colupulone with a purity of 98.6%. $^1$H NMR (500 MHz, DMSO-d6): δ (ppm) 3.94-4.01 (m, 1H), 2.39 (t, 2H), 1.78-1.82 (m, 4H), 1.47-1.51 (m, 1H), 1.28-1.35 (m, 4H), 1.11 (q, 6H), 0.95-1.01 (m, 4H), 0.91 (d, 18H); LC-MS (ESI, pos. ion) m/z: 407 $[M+H]^+$ A3.2: Preparation of Hexahydro-Lupulone

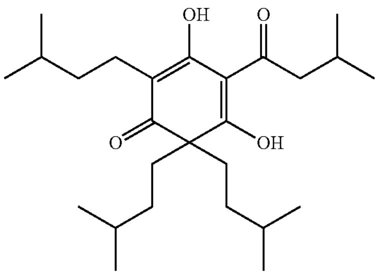 [SMILES: CC(C)CCC1=C(O)C(C(=O)CC(C)C)=C(O)C(CCC(C)C)(CCC(C)C)C1=O]

Hexahydro-lupulone, with a purity of 99.1%, was obtained from hexahydro-β-acids by preparative chromatography. $^1$H NMR (500 MHz, DMSO-d6): δ (ppm) 3.86-3.90 (m, 1H), 2.39 (t, 2H), 1.80-1.83 (m, 4H), 1.59-1.60 (m, 2H), 1.47-1.52 (m, 5H), 1.11 (d, 3H), 0.90-0.96 (m, 7H), 0.86 (d, 18H); LC-MS (ESI, pos. ion) m/z: 421 $[M+H]^+$ A3.3: Preparation of Hexahydro-Adlupulone

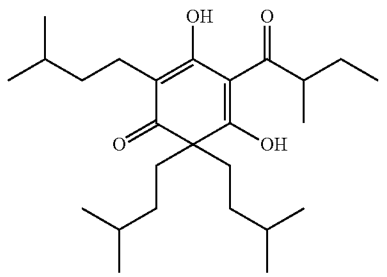 [SMILES: CCC(C)C(=O)C1=C(O)C(CCC(C)C)(CCC(C)C)C(=O)C(CCC(C)C)=C1O]

Hexahydro-adlupulone, with a purity of 98.9%, was obtained from hexahydro-β-acids by preparative chromatography. $^1H$ NMR (500 MHz, DMSO-d6): δ (ppm) 2.82-2.84 (m, 2H), 2.37-2.40 (m, 2H), 2.00-2.05 (m, 1H), 1.80-1.88 (m, 4H), 1.77-1.80 (m, 1H), 1.34-1.51 (q, 2H), 1.29-1.33 (m, 2H), 0.90-0.96 (m, 4H), 0.86-0.90 (m, 24H); LC-MS (ESI, pos. ion) m/z: 421 $[M+H]^+$ A4: Preparation of Prodrugs of Hexahydro-β-Acid Compounds A4.1: Preparation of Hexahydro-Colupulone Mono-Acetate

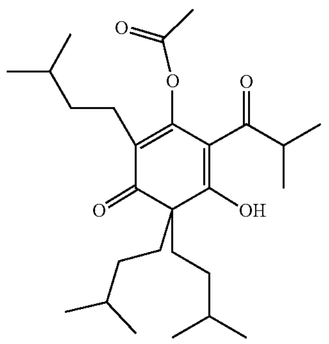 [SMILES: CC(=O)OC1=C(CCC(C)C)C(=O)C(CCC(C)C)(CCC(C)C)C(O)=C1C(=O)C(C)C]

Hexahydro-colupulone (2.0 g, 4.92 mmol, 1.0 eq) was dissolved in 10 mL of dichloromethane, followed by the addition of 0.59 g (5.90 mmol, 1.2 eq) of triethylamine; the mixture was cooled to −5° C.-0° C. with stirring. 0.47 g (5.90 mmol, 1.2 eq) of acetyl chloride was dissolved in 2 mL of dichloromethane; the resulting solution was added slowly and dropwise to the reaction system. Then the resulting reaction mixture was warmed to room temperature, and the reaction was monitored to endpoint by thin-layer chromatography. 5 mL of pure water was added to the reaction mixture, and the organic phase was separated after stirring, washed with water (15 mL×3), dried over anhydrous sodium sulfate, and concentrated by vacuum evaporation to remove organic solvents to give 1.35 g of oily product, with a yield of 61.3%.

A4.2: Preparation of Hexahydro-Colupulone Mono-Propionate

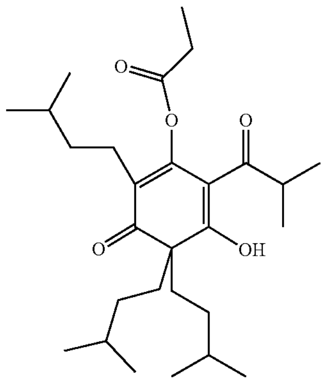 [SMILES: CCC(=O)OC1=C(CCC(C)C)C(=O)C(CCC(C)C)(CCC(C)C)C(O)=C1C(=O)C(C)C]

Hexahydro-colupulone (2.0 g, 4.92 mmol, 1.0 eq) was dissolved in 10 mL of dichloromethane, followed by the addition of 0.48 g (5.90 mmol, 1.2 eq) of triethylamine; the mixture was cooled to −5° C.-0° C. with stirring. 0.55 g (5.90 mmol, 1.2 eq) of propionyl chloride was dissolved in 3 mL of dichloromethane and added slowly and dropwise to the reaction system. The resulting reaction system was warmed to room temperature and the reaction was monitored to endpoint by thin-layer chromatography. 5 mL of pure water was added to the reaction system, and an organic phase was separated after stirring, washed with water (15 mL×3), dried over anhydrous sodium sulfate, and concentrated by vacuum evaporation to remove organic solvents to give 1.52 g of oily product, with a yield of 66.8%.

A4.3: Preparation of Hexahydro-Colupulone Mono-Butyrate

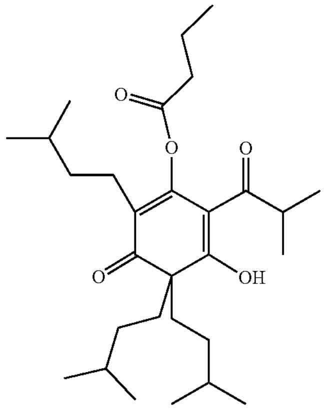 [SMILES: CCCC(=O)OC1=C(CCC(C)C)C(=O)C(CCC(C)C)(CCC(C)C)C(O)=C1C(=O)C(C)C]

Hexahydro-colupulone (2.0 g, 4.92 mmol, 1.0 eq) was dissolved in 10 mL of dichloromethane, followed by the addition of 0.60 g (5.90 mmol, 1.2 eq) of triethylamine; the mixture was cooled to −5° C.-0° C. with stirring. 0.62 g (5.90 mmol, 1.2 eq) of butyryl chloride was dissolved in 3 mL of dichloromethane and added slowly and dropwise to the reaction system. The resulting reaction system was warmed to room temperature and the reaction was monitored to endpoint by thin-layer chromatography. 5 mL of pure water was added to the reaction system, and an organic phase was separated after stirring, washed with water (15 mL×3), dried over anhydrous sodium sulfate, and concentrated by vacuum evaporation to remove organic solvents to give 1.29 g of oily product, with a yield of 55.1%.

A4.4: Preparation of Hexahydro-Colupulone Di-Propionate

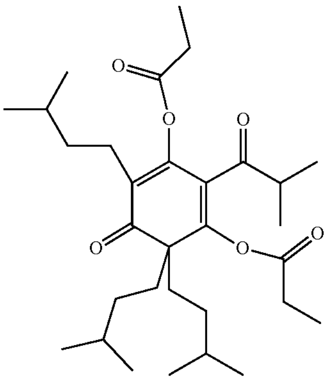 [SMILES: CCC(=O)OC1=C(CCC(C)C)C(=O)C(CCC(C)C)(CCC(C)C)C(OC(=O)CC)=C1C(=O)C(C)C]

Hexahydro-colupulone (2.5 g, 6.15 mmol, 1.0 eq) was placed in a 50 mL dry reaction vessel. Discharged oxygen and moisture by nitrogen, to the vessel were sequentially added 20 mL of n-heptane and 0.1 g (0.82 mmol, 0.13 eq) of 4-dimethylaminopyridine. The reaction system was cooled to 0° C., and then to the resulting reaction system were sequentially added dropwise 1.37 g (14.76 mmol, 2.4 eq) of propionyl chloride and 1.49 g (14.76 mmol, 2.4 eq) of triethylamine The resulting reaction system was stirred and the reaction was monitored to the endpoint by thin-layer chromatography. The reaction solution was filtered to remove triethylamine hydrochloride, and then concentrated by vacuum evaporation to remove solvents to give a yellow and oily crude product. The crude product was subjected to silica gel column chromatography (dichloromethane/methanol (w/w)=10/1) to give 1.39 g of hexahydro-colupulone di-propionate with a yield of 43.7%.

A4.5: Preparation of Hexahydro-Colupulone Di-Butyrate

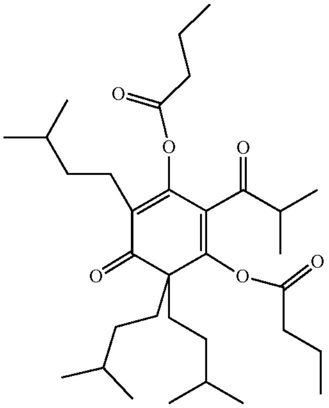 [SMILES: CCCC(=O)OC1=C(CCC(C)C)C(=O)C(CCC(C)C)(CCC(C)C)C(OC(=O)CCC)=C1C(=O)C(C)C]

Hexahydro-colupulone (2.5 g, 6.15 mmol, 1.0 eq) was placed in a 50 mL dry reaction vessel. Discharged oxygen and moisture by nitrogen, to the vessel were sequentially added 20 mL of n-heptane and 0.1 g (0.82 mmol, 0.13 eq) of 4-dimethylaminopyridine. The reaction system was cooled to 0° C., and then to the resulting reaction system were sequentially added dropwise 1.57 g (14.76 mmol, 2.4 eq) of butyryl chloride and 1.49 g (14.76 mmol, 2.4 eq) of triethylamine. The resulting system was stirred and the reaction was monitored to endpoint by thin-layer chromatography. The resulting reaction solution was filtered to remove triethylamine hydrochloride, and then concentrated by vacuum evaporation to remove solvents to give a yellow and oily crude product. The crude product was subjected to silica gel column chromatography (dichloromethane/methanol (w/w)=10/1) to give 1.59 g of hexahydro-colupulone di-butyrate with a yield of 47.2%.

A4.6: Preparation of Hexahydro-Adlupulone Mono-Propionate

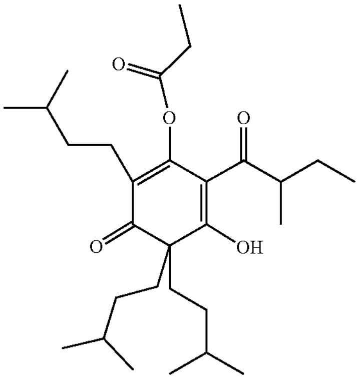 [SMILES: CCC(=O)OC1=C(CCC(C)C)C(=O)C(CCC(C)C)(CCC(C)C)C(O)=C1C(=O)C(C)CC]

Hexahydro-adlupulone (2.5 g, 5.94 mmol, 1.0 eq) was dissolved in 15 mL of dichloromethane, followed by the addition of 0.72 g (7.13 mmol, 1.2 eq) of triethylamine; the mixture was to cooled to −5° C.-0° C. with stirring. 0.66 g (7.13 mmol, 1.2 eq) of propionyl chloride was dissolved in 6 mL of dichloromethane and added slowly and dropwise to the reaction system. The resulting reaction system was warmed to room temperature and the reaction was monitored to endpoint by thin-layer chromatography. 5 mL of pure water was added to the reaction system, and the organic phase was separated after stirring, washed with water (20 mL×3), dried over anhydrous sodium sulfate, and concentrated by vacuum evaporation to remove organic solvents to give 1.66 g of oily product, with a yield of 58.5%.

A4.7: Preparation of Hexahydro-Adlupulone Mono-Butyrate

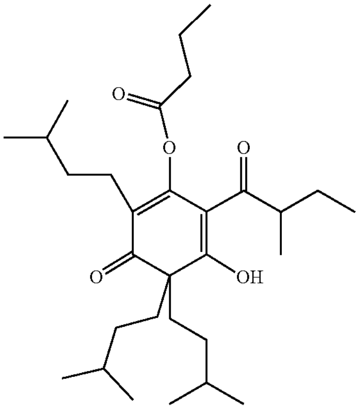 [SMILES: CCCC(=O)OC1=C(CCC(C)C)C(=O)C(CCC(C)C)(CCC(C)C)C(O)=C1C(=O)C(C)CC]

Hexahydro-adlupulone (2.5 g, 5.94 mmol, 1.0 eq) was dissolved in 15 mL of dichloromethane, followed by the addition of 0.72 g (7.13 mmol, 1.2 eq) of triethylamine; the mixture was cooled to −5° C.-0° C. with stirring. 0.76 g (7.13 mmol, 1.2 eq) of butyryl chloride was dissolved in 8 mL of dichloromethane and added slowly and dropwise to the reaction system. The resulting reaction system was warmed to room temperature and the reaction was monitored to endpoint by thin-layer chromatography. 6 mL of pure water was added to the reaction system, and the organic phase was separated after stirring, washed with water (30 mL×3), dried over anhydrous sodium sulfate, and concentrated by vacuum evaporation to remove organic solvents to give 1.45 g of oily product, with a yield of 49.6%.

A4.8: Preparation of Hexahydro-Adlupulone Di-Propionate

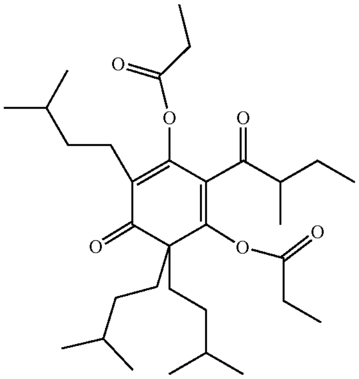 [SMILES: CCC(=O)OC1=C(CCC(C)C)C(=O)C(CCC(C)C)(CCC(C)C)C(OC(=O)CC)=C1C(=O)C(C)CC]

Hexahydro-adlupulone (2.5 g, 5.94 mmol, 1.0 eq) was placed in a 50 mL dry reaction vessel. Discharged oxygen and moisture by nitrogen, to the vessel were sequentially added 25 mL of n-heptane and 0.15 g (0.82 mmol, 0.14 eq) of 4-dimethylaminopyridine. The reaction system was cooled to 0° C., and then to the reaction system were sequentially added dropwise 1.32 g (14.26 mmol, 2.4 eq) of propionyl chloride and 1.44 g (14.26 mmol, 2.4 eq) of triethylamine. The resulting reaction system was stirred and the reaction was monitored to endpoint by thin-layer chromatography. The resulting reaction solution was filtered to remove triethylamine hydrochloride, and then concentrated by vacuum evaporation to remove solvents to give a yellow and oily crude product. The crude product was subjected to silica gel column chromatography (dichloromethane/methanol (w/w)=10/1), to give 1.42 g of hexahydro-adlupulone di-propionate with a yield of 44.9%.

A4.9: Preparation of Hexahydro-Adlupulone Di-Butyrate

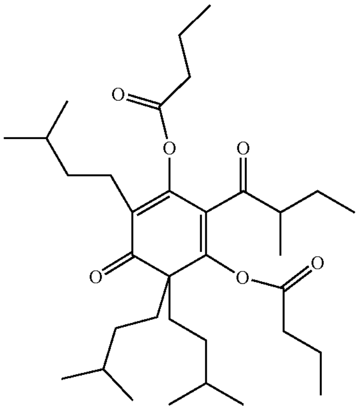 [SMILES: CCCC(=O)OC1=C(CCC(C)C)C(=O)C(CCC(C)C)(CCC(C)C)C(OC(=O)CCC)=C1C(=O)C(C)CC]

Hexahydro-adlupulone (2.5 g, 5.94 mmol, 1.0 eq) was placed in a 50 mL dry reaction vessel. Discharged oxygen and moisture by nitrogen, to the vessel were sequentially added 25 mL of n-heptane and 0.1 g (0.82 mmol, 0.14 eq) of 4-dimethylaminopyridine. The reaction system was cooled to 0° C., and then to the reaction system were sequentially added dropwise 1.52 g (14.26 mmol, 2.4 eq) of butyryl chloride and 1.44 g (14.26 mmol, 2.4 eq) of triethylamine. The resulting reaction system was stirred and the reaction was monitored to endpoint by thin-layer chromatography. The resulting reaction solution was filtered to remove triethylamine hydrochloride, and then concentrated by vacuum evaporation to remove solvents to give a yellow and oily crude product. The crude product was subjected to silica gel column chromatography (dichloromethane/methanol (w/w)=10/1) to give 1.72 g of hexahydro-adlupulone di-butyrate with a yield of 51.7%.

A4.10: Preparation of Hexahydro-Colupulone Mono-Decanoate

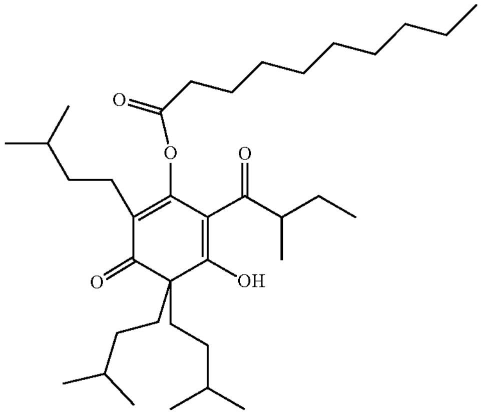 [SMILES: CCCCCCCCCC(=O)OC1=C(CCC(C)C)C(=O)C(CCC(C)C)(CCC(C)C)C(O)=C1C(=O)C(C)CC]

Hexahydro-colupulone (2.5 g, 6.15 mmol, 1.0 eq) was dissolved in 10 mL of dichloromethane, followed by the addition of 0.75 g (7.38 mmol, 1.2 eq) of triethylamine; the mixture was cooled to −5° C.-0° C. with stirring. 1.41 g (7.38 mmol, 1.2 eq) of decanoyl chloride was dissolved in 8 mL of dichloromethane and added slowly and dropwise to the reaction system. The resulting reaction system was warmed to room temperature and the reaction was monitored to endpoint by thin-layer chromatography. 5 mL of pure water was added to the reaction system, and the organic phase was separated after stirring, washed with water (15 mL×3), dried over anhydrous sodium sulfate, decolorized by silica gel, and concentrated by vacuum evaporation to remove organic solvents to give 1.87 g of oily product, with a yield of 54.2%.

A4.11: Preparation of Hexahydro-Colupulone Mono-Laurate

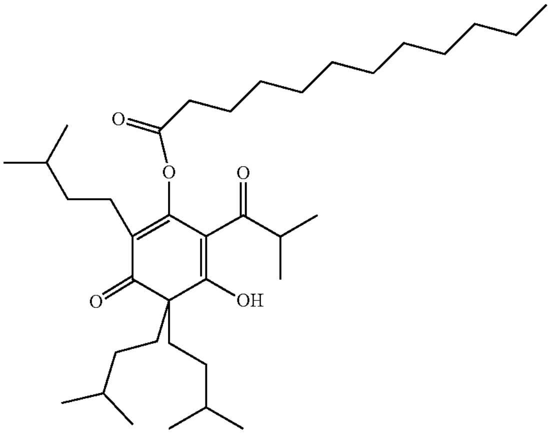 [SMILES: CCCCCCCCCCCC(=O)OC1=C(CCC(C)C)C(=O)C(CCC(C)C)(CCC(C)C)C(O)=C1C(=O)C(C)C]

Hexahydro-colupulone (2.5 g, 6.15 mmol, 1.0 eq) was dissolved in 10 mL of dichloromethane, followed by the addition of 0.75 g (7.38 mmol, 1.2 eq) of triethylamine; the mixture was cooled to −5° C.-0° C. with stirring. 1.61 g (7.38 mmol, 1.2 eq) of lauroyl chloride was dissolved in 8 mL of dichloromethane and added slowly and dropwise to the reaction system. The resulting reaction system was warmed to room temperature and the reaction was monitored to endpoint by thin-layer chromatography. 5 mL of pure water was added to the reaction system, and the organic phase was separated after stirring, washed with water (15 mL×3), dried over anhydrous sodium sulfate, and concentrated by vacuum evaporation to remove organic solvents to give a crude product. The crude product was subjected to silica gel column chromatography (dichloromethane/methanol (w/w)=10/0.8) to give 2.00 g of oily product, with a yield of 55.3%.

Note: Methods for the preparation of hexahydro-colupulone mono-pentanoate and hexahydro-colupulone mono-hexanoate were identical to the method for the preparation of hexahydro-colupulone mono-butyrate.

Example B: Preparation of Feed Compositions of the Prodrugs of Hexahydro-β-Acid Compounds In the feed compositions provided herein, the content of a prodrug of a hexahydro-β-acid compound is not less than 0.00001%, and can be adjusted according to the need for nutrients of an animals at various growth stages or usability of the properties of a product in feed industry (such as additives for feed, ingredients for feed additive, ingredients for feed), and can also be adjusted according to the weight ratio of other nutritional substances and non-nutritional substances in different feed formulas to meet the need of the feed formulas. The feed compositions herein will be further described below with basic granular premixes as examples; however, any replacements or additions of the components of a formula or any similar formulas are deemed consistent with the purpose of the present invention, wherein the components of a formula are used to achieve a non-synergistic effect on each other.

The method of the preparation of a feed composition: Ingredient(s) and adjuvant(s) were evenly mixed in a mixer. The resulting mixture and an aqueous solution of 1.3% (wt) hydroxypropyl methylcellulose at a ratio of 100:35 were put into a pellet mill where the mixing and cutter process was operated for 3-5 minutes. After pelleting is complete, the product was dried in fluid bed for 30 minutes and then passed through 16-mesh sieves.

Ingredients: The prodrugs of a hexahydro-β-acid compound prepared in Example A

Adjuvants (carriers): Corn starch

Formulas: As shown in Table 1

TABLE 1

Formula of an additive for a feed as granular

| Product | Ingredients/ Weight | Carrier/ Weight | Adhesive/ Weight |
|---|---|---|---|
| Composition 1 | Hexahydro-colupulone/1 | 99 | 35 |
| Composition 2 | Hexahydro-adlupulone/1 | 99 | 35 |
| Composition 3 | Hexahydro-colupulone mono-acetate/1 | 99 | 35 |
| Composition 4 | Hexahydro-colupulone mono-propionate/1 | 99 | 35 |
| Composition 5 | Hexahydro-colupulone mono-butyrate/1 | 99 | 35 |
| Composition 6 | Hexahydro-adlupulone mono-propionate/1 | 99 | 35 |
| Composition 7 | Hexahydro-adlupulone mono-butyrate/1 | 99 | 35 |
| Composition 8 | Hexahydro-colupulone mono-decanoate/1 | 99 | 35 |
| Composition 9 | Hexahydro-colupulone mono-laurate/1 | 99 | 35 |
| Composition 10 | Hexahydro-colupulone di-propionate/1 | 99 | 35 |
| Composition 11 | Hexahydro-colupulone di-butyrate/1 | 99 | 35 |
| Composition 12 | Hexahydro-colupulone mono-propionate/ hexahydro-adlupulone mono-propionate (w/w = 1:0.5)/1 | 99 | 35 |
| Composition 13 | Hexahydro-colupulone mono-propionate/ hexahydro-adlupulone mono-propionate (w/w = 1:0.25)/1 | 99 | 35 |

Example C: Study on Thermal Stability and Photostability of the Prodrugs of Hexahydro-β-Acid Compounds 1: Materials Equipment and reagents: Drug stability testing chamber; High Performance Liquid Chromatography (HPLC); methanol (chromatographic grade); phosphoric acid (analytical grade).

Ingredients for testing: Hexahydro-colupulone; hexahydro-colupulone mono-acetate; hexahydro-colupulone mono-propionate; hexahydro-colupulone mono-butyrate.

2: Experiment 2.1: Preparation of Samples, and Experimental Methods

Preparation of a sample of 1% premix of an ingredient: 1 g of an ingredient was respectively weighed out and evenly mixed with 99 g of corncob meal in a mixer to give a sample of 1% premix of an ingredient for testing.

Thermal stability testing at 60° C.: The samples of an ingredient and 1% premix thereof were respectively spread in petri dishes to form thin layers of <5 mm, and kept at 60° C. Two replications for a sample were taken in parallel on day 5 and day 10 for HPLC analysis. Results were shown in Table 2.

Photostability testing: The samples of an ingredient and 1% premix thereof were respectively spread in petri dishes to form thin layers of <5 mm, and kept under an illumination of 4500 Lx. Three replications for a sample were sampled in parallel on day 5 and day 10 for HPLC analysis. Results were shown in Table 2.

2.2: Preparation of Standard Solutions 25.0 mg of an ingredient was accurately weighed out and dissolved in an appropriate amount of methanol by ultrasonication. The solution was then transferred to a volumetric flask and diluted to 25 mL with methanol to give a stock solution. The samples from the stock solution were diluted with methanol respectively to a concentration of 100 ppm, 500 ppm, and 1000 ppm of work solution, and then the working solutions were filtered by 0.22 μm organic membranes. Between the concentration of a sample and the response value of HPLC peak area thereof, the linearity was adjusted and detected to give a standard curve.

2.3: Preparation of Sample Solution 25.0 mg of an ingredient and 2.0000 g of a sample of 1% premix thereof were respectively accurately weighed out, and dissolved in 25 mL of methanol by ultrasonication for 10 minutes. The resulting solutions were filtered by organic membranes and then analyzed by HPLC.

2.4: Testing Conditions for HPLC

Column: Symmetry Cis column (Waters; 250 mm*4.6 mm, 5 μm).

Mobile phase: 0.02% phosphoric acid:methanol=5:95 (v:v).

Wavelength: 235 nm.

Temperature of the Column: 25° C.

Injection volume: 10 μL.

Flow rate: 1 mL/min.

3: Results

As shown in Table 2, as an active ingredient of 1% premix, a change of hexahydro-colupulone was more than 5% in the 10-day testing period of thermal stability testing at 60° C., and more than 15% in the photostability testing on day 10. The change of each of hexahydro-colupulone mono-acetate, mono-propionate and mono-butyrate, no matter as an ingredient or as an active ingredient in premix, was not more than 5% in both of the thermal stability testing and photostability testing. It was shown that the short-chain aliphatic acid ester derivatives achieved an effect of thermal stability and photostability to meet the requirements of an additive for a feed.

TABLE 2

Results of the study on the factors of stability of ester derivatives of hexahydro-colupulone and 1% premixes thereof

| Item | | Sample | Residual amount of active ingredient/% Day 5 | Day 10 |
|---|---|---|---|---|
| Stability testing at 60° C. | Ingredient | hexahydro-colupulone mono-acetate | 99.69 | 99.44 |
| | | hexahydro-colupulone mono-propionate | 99.40 | 99.26 |
| | | hexahydro-colupulone mono-butyrate | 99.76 | 99.64 |
| | | hexahydro-colupulone | 99.76 | 99.10 |
| | 1% Premix of an ingredient | hexahydro-colupulone mono-acetate | 99.40 | 98.68 |
| | | hexahydro-colupulone mono-propionate | 98.27 | 97.91 |
| | | hexahydro-colupulone mono-butyrate | 98.21 | 97.57 |
| | | hexahydro-colupulone | 97.02 | 93.56 |
| Photostability testing | Ingredient | hexahydro-colupulone mono-acetate | 98.97 | 98.31 |
| | | hexahydro-colupulone mono-propionate | 98.90 | 98.70 |
| | | hexahydro-colupulone mono-butyrate | 99.99 | 99.10 |
| | | hexahydro-colupulone | 92.71 | 85.66 |
| | 1% Premix of an ingredient | hexahydro-colupulone mono-acetate | 99.28 | 98.82 |
| | | hexahydro-colupulone mono-propionate | 98.87 | 98.10 |
| | | hexahydro-colupulone mono-butyrate | 99.14 | 98.08 |
| | | hexahydro-colupulone | 90.11 | 83.62 |

Note:
Residual amount of active ingredient refers to a percentage of the detected content of the active ingredient on day n relative to the content on day 0 during the experiment.

Example D: Study on Long-Term Stability of a Prodrug of a Hexahydro-β-Acid Compound in a Feed 1: Materials Equipment and reagents: Drug stability testing chamber; High Performance Liquid Chromatography (HPLC); methanol (chromatographic grade); phosphoric acid (analytical grade); n-hexane (chromatographic grade); isopropanol (chromatographic grade).

Ingredients for testing: Hexahydro-colupulone; hexahydro-colupulone mono-acetate; hexahydro-colupulone mono-propionate; hexahydro-colupulone mono-butyrate; hexahydro-colupulone mono-pentanoate (provided by Chemistry Department of Guangzhou Insighter Biotechnology Co., Ltd); hexahydro-colupulone mono-hexanoate (provided by Chemistry Department of Guangzhou Insighter Biotechnology Co., Ltd); hexahydro-colupulone mono-laurate; disodium salt of hexahydro-colupulone mono-phosphate (provided by Chemistry Department of Guangzhou Insighter Biotechnology Co., Ltd); hexahydro-colupulone mono-phosphate diethyl ester (provided by Chemistry Department of Guangzhou Insighter Biotechnology Co., Ltd).

Feeds: ZUSF's premixed feed (A mixture of crushed Feed A and crushed Feed B at a weight ratio of 2:1, wherein Feed A was a 5.33% multi-premixed feed for piglets from ZUSF's Hao-Ru-Zhen-Jing, and B was a 2.67% multi-premixed feed for piglets from ZUSF's Hao-Ru-Zhen-Jing); creep feed for piglets from CP FEED; INSIGHTER's feed for broiler; 4% premixed feed from GUANGDONG CO-POWER.

2: Experiment 2.1: Preparation of Samples, and Experimental Methods

Preparation of a sample of 1% premix of Ingredient: 1 g of an ingredient was respectively weighed out and evenly mixed with 99 g of corncob meal in a mixer to give a sample of 1% premix of an ingredient.

Preparation of a sample of 500 ppm feed of an ingredient: The sample of 1% premix of an ingredient was diluted step by step using the ZUSF's remixed feed to 5000 ppm and 500 ppm to give the sample of 500 ppm feed of an ingredient for later testing.

Preparation of a sample of 100 ppm feed of an ingredient: sample of 1% premix of an ingredient was diluted step by step using the creep feed for piglets from CP FEED to 1000 ppm and then 100 ppm to give the sample of 100 ppm feed of an ingredient for later testing.

Preparation of a sample of 100 ppm feed of an ingredient: The sample of 1% premix of an ingredient was diluted step by step using the INSIGHTER's feed for broiler to 1000 ppm and 100 ppm to give the sample of 100 ppm feed of an ingredient for later testing.

Preparation of a sample of 2000 ppm feed of an ingredient: The sample of 1% premix of an ingredient was diluted step by step using the 4% premixed feed from GUANGDONG CO-POWER to 5000 ppm and 2000 ppm to give the sample of 2000 ppm feed of an ingredient for later testing.

Method: Three replications of each feed sample were tested at the condition of 25° C.±2° C. and RH 60%±10%, wherein the replications of each feed sample were sampled in parallel for HPLC analysis on day 5, day 10, day 15, day 30, day 60, and day 90. Results were shown in Table 3.

2.2: Preparation of Standard Solutions 25.0 mg of an ingredient was accurately weighed out and dissolved in an appropriate amount of methanol or n-hexane by ultrasonication. The solution was then transferred to a volumetric flask and diluted to 50 mL to give a 500 ppm (by wt.) stock solution. The samples from the stock solution were diluted with methanol or n-hexane respectively to a concentration of 10 ppm, 25 ppm, 50 ppm, 100 ppm, and 250 ppm of work solution, and then the working solutions were filtered by 0.22 μm organic membranes. Between the concentration of a sample and the response value of HPLC peak area thereof, the linearity was adjusted and detected to give a standard curve.

2.3: Preparation of Sample Solutions 5.0000 g of the samples sampled at different time intervals were respectively accurately weighed out, and dissolved in 25 mL of methanol or n-hexane by ultrasonication for 10 minutes. The resulting solutions were filtered by organic membranes and then analyzed by HPLC.

2.4: Testing Conditions for HPLC

Reversed Phase Chromatography:

Equipment: Waters e2695 with PDA detector.

Mobile phase: 0.02% phosphoric acid:methanol=5:95 (v:v).

Column: Symmetry Cis column (Waters; 250 mm×4.6 mm, 5 μm).

Wavelength: 235 nm.

Temperature of the Column: 25° C.

Injection volume: 10 μL.

Flow rate: 1 mL/min.

Normal Phase Chromatography:

Equipment: Shimadzu LC-14C/SPD-15C.

Column: SuperSil NH2 column (5 m; 250 mm×4.6 mm).

Mobile phase: n-hexane:isopropanol=60:40 (v:v).

Wavelength: 235 nm.

Temperature of the Column: 25° C.

Injection volume: 20 μL.

Flow rate: 1 mL/min.

3: Results

As shown in Table 3:

During the testing period, the content of hexahydro-colupulone in feed for 30 day decreased substantially, and that of the phosphate derivatives of hexahydro-colupulone in the feeds decreased substantially at the beginning of the testing. The aliphatically esterified derivatives of hexahydro-colupulone maintained good stability at room temperature, wherein the stability of hexahydro-colupulone mono-acetate, mono-pentanoate, and mono-hexanoate were relatively poor in some of the feeds.

TABLE 3

Stability testing of ester derivatives of hexahydro-colupulone in feeds at room temperature

| Concentration | | Sample | Residual amount of active ingredient/% Day 5 | Day 15 | Day 30 | Day 60 | Day 90 |
|---|---|---|---|---|---|---|---|
| 100 ppm | INSIGHTER's broiler feed | hexahydro-colupulone mono-acetate | 94.93 | 81.77 | 72.30 | 71.97 | — |
| | | hexahydro-colupulone mono-propionate | 99.45 | 99.37 | 99.19 | 99.72 | — |
| | | hexahydro-colupulone mono-butyrate | 99.00 | 98.79 | 98.39 | 98.11 | — |
| | | hexahydro-colupulone mono-pentanoate | 98.84 | 98.12 | 97.73 | 96.64 | — |
| | | hexahydro-colupulone mono-hexanoate | 98.90 | 97.72 | 96.58 | 95.77 | — |
| | | hexahydro-colupulone mono-laurate | 99.63 | 99.65 | 99.68 | 98.68 | 98.47 |
| | | disodium salt of hexahydro-colupulone mono-phosphate | 86.64 | 83.77 | 81.32 | 76.53 | 62.97 |
| | | hexahydro-colupulone mono-phosphate diethyl ester | 92.76 | 89.33 | 82.46 | 79.05 | 77.29 |
| | Creep feed for piglets from CP FEED | hexahydro-colupulone mono-acetate | 97.69 | 96.27 | 96.22 | 96.16 | 95.08 |
| | | hexahydro-colupulone mono-propionate | 100.54 | 100.97 | 97.62 | 98.08 | 96.99 |
| | | hexahydro-colupulone mono-butyrate | 98.19 | 96.62 | 95.70 | 95.47 | 95.77 |
| | | hexahydro-colupulone mono-pentanoate | 100.94 | 98.82 | 96.92 | 96.01 | 95.61 |

TABLE 3-continued

Stability testing of ester derivatives of hexahydro-colupulone in feeds at room temperature

| Concentration | | Sample | Residual amount of active ingredient/% Day 5 | Day 15 | Day 30 | Day 60 | Day 90 |
|---|---|---|---|---|---|---|---|
| | | hexahydro-colupulone mono-hexanoate | 102.18 | 96.14 | 95.30 | 95.20 | 95.55 |
| | | hexahydro-colupulone | 98.28 | 96.93 | 93.07 | 77.54 | 68.28 |
| | | disodium salt of hexahydro-colupulone mono-phosphate | 66.59 | 58.39 | 55.80 | 47.76 | 44.33 |
| | | hexahydro-colupulone mono-phosphate diethyl ester | 85.27 | 78.06 | 69.43 | 60.04 | 53.77 |
| 1000 ppm | INSIGHTER's broiler feed | hexahydro-colupulone mono-laurate | 101.19 | 101.72 | 98.60 | 97.85 | 95.26 |
| 2000 ppm | 4% premixed feed from GUANGDONG CO-POWER | hexahydro-colupulone mono-propionate | 97.48 | 96.12 | 96.28 | 95.87 | 95.90 |
| | | hexahydro-colupulone mono-butyrate | 98.62 | 95.56 | 95.48 | 96.34 | 95.41 |
| 500 ppm | ZUSF's premixed feed | hexahydro-colupulone mono-acetate | 96.65 | 96.65 | 96.84 | 95.23 | 85.29 |
| | | hexahydro-colupulone mono-propionate | 98.36 | 96.77 | 94.17 | 95.88 | 95.73 |
| | | hexahydro-colupulone mono-butyrate | 100.31 | 98.23 | 96.01 | 96.13 | 95.29 |
| | | hexahydro-colupulone mono-pentanoate | — | 94.29 | 94.80 | 88.17 | 89.14 |
| | | hexahydro-colupulone mono-hexanoate | — | 87.50 | 89.00 | 86.07 | 83.77 |

Note:
Residual amount of active ingredient refers to the percentage of the detected content of the active ingredient on day n relative to the content on day 0.
The symbol "—" means that no test was conducted.

Example E: Effect of the Prodrugs of Hexahydro-β-Acid Compounds on the Production Performance of Hogs 480 67-day-old Duroc×Landrace×Yorkshire cross-bred bacon-type piglets with similar body weight, were randomly divided into 16 groups, with 3 replications per group, 10 piglets per replication and equal amounts of males and females. The pig pen and tools were sterilized before the trial. In the trial, the piglets were kept in separate regions in the same pig pen under the same feeding and management conditions, were given a free hand with the feed and the water, and were fed twice a day. The groups were known as control group (group 1) and test groups 2 to 16. The piglets of the control group were fed with basal formula feed only, while those of the test groups 2 to 16 were respectively fed with basal formula feed mixed with different additives, wherein the active ingredient of the additives was a hexahydro-β-acid compound or a prodrug of a hexahydro-β-acid compound provide herein, and the content thereof in the feed was 5 or 25 ppm as shown in Table 4.

The trial lasted for 14 days. During the trial, each test group was not fed with other antioxidants or growth enhancers. On the 14th day, each test group was fed with no feed but water for 12 hours, and the piglets of each replication as one unit were weighed to calculate the average daily feed intake (ADFI, g/d per piglet), the average daily weight gain (ADG, g/d per piglet), and the feed conversion ratio (FCR).

Average daily feed intake=(Total weight of provided feed−Weight of residual feed)/(Days of the trial×Number of piglets in each replicate)

Average daily weight gain=(final average body weight−initial average body weight)/Days of the trial Feed conversion ratio=average daily feed intake/average daily weight gain Results were shown in Table 4.

TABLE 4

Effect of hexahydro-β-acid compounds and prodrugs thereof on production performance of hogs

| Group | Active Ingredient of the Additive | ADFI (g/d per piglet) | ADG (g/d per piglet) | FCR |
|---|---|---|---|---|
| 1 | — | 873 | 358 | 2.437 |
| 2 | Hexahydro-colupulone; 25 ppm | 894 | 403 | 2.218 |
| 3 | Hexahydro-adlupulone; 25 ppm | 860 | 384 | 2.240 |
| 4 | Hexahydro-colupulone mono-acetate; 5 ppm | 860 | 368 | 2.340 |
| 5 | Hexahydro-colupulone mono-acetate; 25 ppm | 960 | 435 | 2.208 |
| 6 | Hexahydro-colupulone mono-butyrate; 5 ppm | 991 | 447 | 2.217 |

TABLE 4-continued

Effect of hexahydro-β-acid compounds and prodrugs thereof on production performance of hogs

| Group | Active Ingredient of the Additive | ADFI (g/d per piglet) | ADG (g/d per piglet) | FCR |
|---|---|---|---|---|
| 7 | Hexahydro-colupulone mono-butyrate; 25 ppm | 973 | 441 | 2.205 |
| 8 | Hexahydro-colupulone mono-hexanoate; 25 ppm | 913 | 383 | 2.386 |
| 9 | Hexahydro-colupulone mono-decanoate; 25 ppm | 895 | 374 | 2.394 |
| 10 | Hexahydro-colupulone mono-laurate; 25 ppm | 918 | 383 | 2.399 |
| 11 | Hexahydro-adlupulone mono-propionate; 25 ppm | 876 | 393 | 2.228 |
| 12 | Hexahydro-adlupulone mono-butyrate; 25 ppm | 883 | 398 | 2.221 |
| 13 | Hexahydro-colupulone di-propionate; 25 ppm | 926 | 415 | 2.231 |
| 14 | Hexahydro-colupulone di-butyrate; 25 ppm | 950 | 413 | 2.298 |
| 15 | Hexahydro-colupulone mono-propionate/ hexahydro-adlupulone mono-propionate (1:0.5); 25 ppm | 974 | 439 | 2.219 |
| 16 | Hexahydro-colupulone/ hexahydro-adlupulone (1:0.5); 25 ppm | 875 | 380 | 2.301 |

Note:
In group 16, the additive "hexahydro-colupulone/hexahydro-adlupulone (1:0.5)" refers to the weight ratio of hexahydro-colupulone to hexahydro-adlupulone in the content of 25 ppm. The definition is also applicable to that of group 15.

As shown in Table 4, effect of the test samples on the production performance of piglets was evaluated in terms of three factors: feed intake, weight gain, and feed efficiency. The feed intakes of piglets in the groups of ester derivatives of hexahydro-colupulone or hexahydro-adlupulone were increased compared to that of piglets in the control group, hexahydro-colupulone group or hexahydro-adlupulone group. At the same content in feed, the mono-acetate derivatives, mono-propionate derivatives, mono-butyrate derivatives of hexahydro-colupulone or hexahydro-adlupulone achieve a substantially identical or better effect on the feed conversion ratio of the piglets, compared to that of hexahydro-colupulone or hexahydro-adlupulone. However, the effects of mono-hexanoate, mono-decanoate, and mono-laurate of hexahydro-colupulone on the performance of piglets were not as significant as the effects of mono-acetate and mono-butyrate thereof, probably due to the incomplete or slow hydrolysis of these ester compounds in the intestinal tract of animals.

Example F: Effect of the Prodrugs of Hexahydro-β-Acid Compounds on the Production Performance of Broilers Single-factor was used to conduct the trial. 540 1-day-old yellow broilers with a similar average body weight of 50 g were randomly divided into 6 groups, with 6 replicates per group, equal amount of males and females and 15 yellow broilers per replicate. The chicken house and tools were sterilized before the trial. During the trial, the broilers were kept in separate regions in the same chicken house under the same feeding and management conditions. During the trial, each test group was fed with basal formula feed consisting of corn and soybean and not fed with other antioxidants or growth enhancers. The groups were known as control group (group 1) and test groups 2 to 6, wherein the control group was fed with basal formula feed only, while the test groups 2 to 6 were fed with basal formula feeds respectively mixed with hexahydro-colupulone, hexahydro-colupulone mono-acetate, or hexahydro-colupulone mono-butyrate, as shown in Table 5.

The trial lasted for 30 days. The broilers were given free hand with feed and water and were fed twice a day. To calculate the average daily feed intake (ADFI, g/d per broiler), the average daily weigh gain (ADG, g/d per broiler) and the feed conversion ratio (FCR), the 31 days old broilers (12 hours without feed but water) of each replication as one unit were weighed, and the amount of the feed consumed thereby was counted.

Feed conversion ratio (FCR)=average daily feed intake/average daily weight gain

Results were as shown in Table 5.

TABLE 5

Effect of the prodrugs of hexahydro-β-acid compounds on the production performance of broilers

| Group | Active Ingredient of the Additive | ADFI (g/d per broiler) | ADG (g/d per broiler) | FCR |
|---|---|---|---|---|
| 1 | — | 49.55 | 23.14 | 2.14 |
| 2 | Hexahydro-colupulone; 20 ppm | 49.68 | 25.19 | 1.97 |

TABLE 5-continued

Effect of the prodrugs of hexahydro-β-acid compounds on the production performance of broilers

| Group | Active Ingredient of the Additive | ADFI (g/d per broiler) | ADG (g/d per broiler) | FCR |
|---|---|---|---|---|
| 3 | hexahydro-colupulone mono-acetate; 2 ppm | 49.13 | 25.67 | 2.02 |
| 4 | hexahydro-colupulone mono-acetate; 20 ppm | 50.06 | 27.36 | 1.95 |
| 5 | hexahydro-colupulone mono-butyrate; 2 ppm | 48.32 | 24.65 | 1.96 |
| 6 | hexahydro-colupulone mono-butyrate; 20 ppm | 49.95 | 25.88 | 1.93 |

As shown in Table 5, effect of the test samples on the production performance of broilers was evaluated in terms of three factors: feed intake, weight gain, and feed efficiency. The effects of hexahydro-colupulone mono-acetate and mono-butyrate on the production performance of broilers achieved were equivalent to that of hexahydro-colupulone.

INDUSTRIAL APPLICABILITY

The prodrugs of hexahydro-colupulone and/or hexahydro-adlupulone provided herein achieved an effect on the production performance of animals substantially identical to hexahydro-colupulone and/or hexahydro-adlupulone. As an active ingredient of a feed composition, the prodrugs of hexahydro-colupulone and/or hexahydro-adlupulone provided herein were used not only to avoid the problems of hexahydro-β-acid compounds such as poor thermal stability during feed pelleting process and the poor stability during long-term storage, but also to achieve an effect on production performance substantially equal to hexahydro-β-acid compounds.

What is claimed is:

1. A prodrug of a hexahydro-β-acid compound of formula (I), or a solvate thereof, or a feed-acceptable salt thereof;

(I)

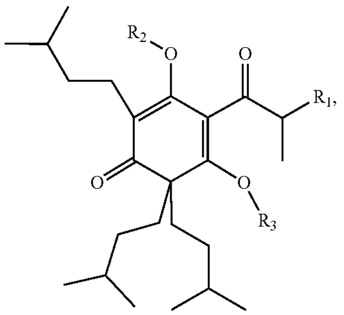

wherein $R_1$ is selected from a substituted or unsubstituted $C_1$-$C_2$ alkyl; and each of $R_2$ and $R_3$ is independently selected from H and a linear or branched $C_2$-$C_4$ carbonyl, wherein the $C_2$-$C_4$ carbonyl is substituted or unsubstituted, with the proviso that $R_2$ and $R_3$ are not both H.

2. The prodrug according to claim 1, wherein each of the $R_2$ and $R_3$ is independently selected from H and $C(=O)CH_2CH_3$.

3. The prodrug according to claim 1, wherein each of the $R_2$ and $R_3$ is independently selected from H and $C(=O)(CH_2)_2CH_3$.

4. The prodrug according to claim 1, wherein the prodrug has one of the formulas below:

(I2-1)

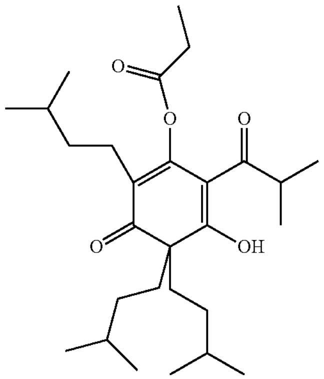

, (I2-2)

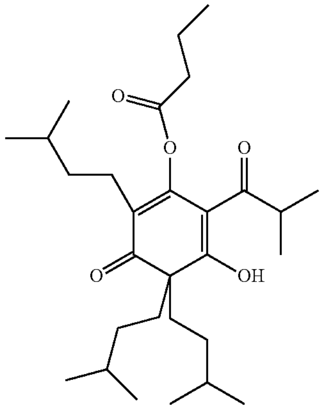

,

-continued
(I2-3)
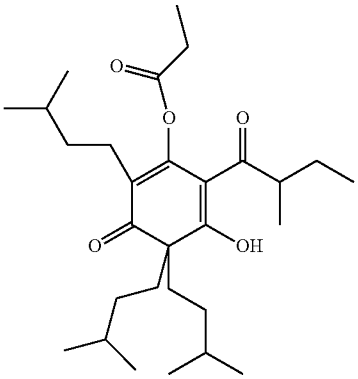
,
(I2-4)
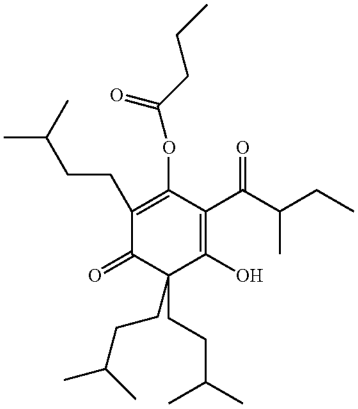
,
(I2-5)
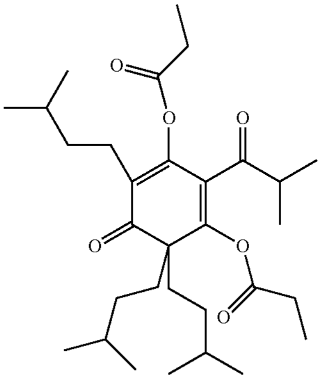
,
(I2-6)
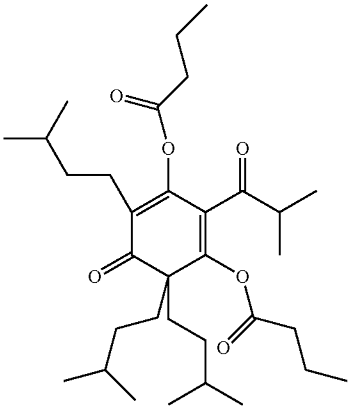
,
-continued
(I2-7)
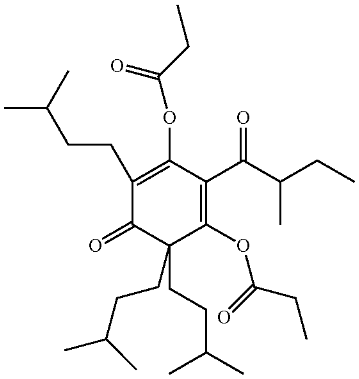
, and
(I2-8)
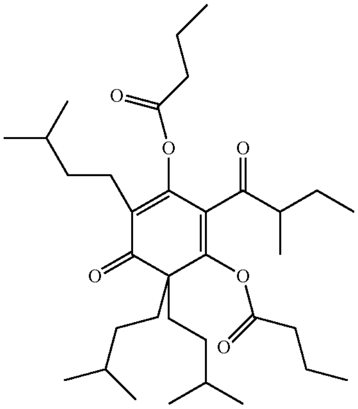
.
5. A feed composition comprising an optional feed-acceptable adjuvant, and the prodrug of claim 1 or a solvate thereof or a feed-acceptable salt thereof.
6. The feed composition according to claim 5, wherein the prodrug has one of formula (I2-1) or formula (I2-2):
(I2-1)
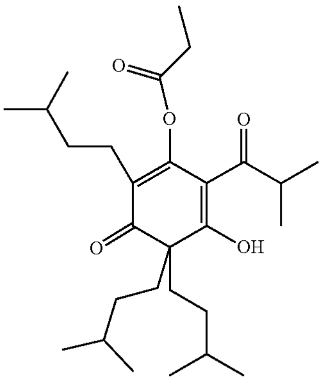
, or -continued
(I2-2)
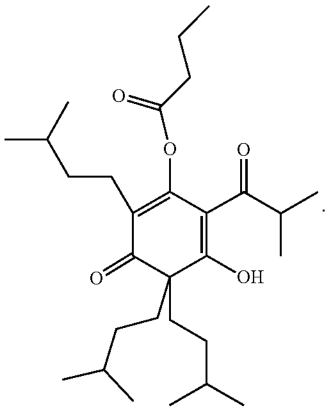
7. The feed composition according to claim 5, wherein the prodrug has one of formula (I2-3) or formula (I2-4):
(I2-3)
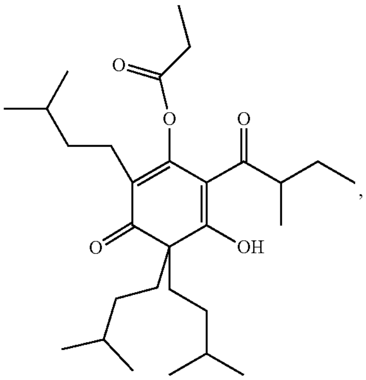
, or
(I2-4)
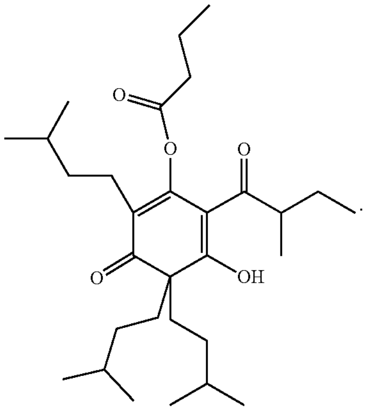
8. The feed composition according to claim 5, wherein the prodrug has one of formula (I2-1) or formula (I2-3):
(I2-1)
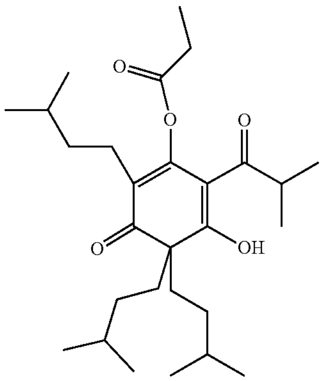
, or
(I2-3)
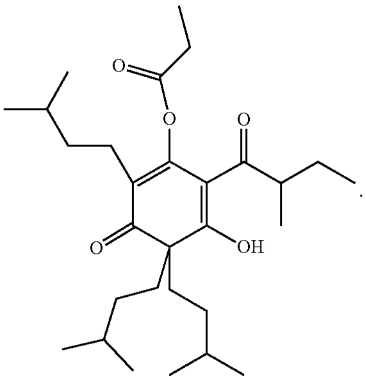
9. The feed composition according to claim 5, wherein the prodrug has one of formula (I2-2) or formula (I2-4):
(I2-2)
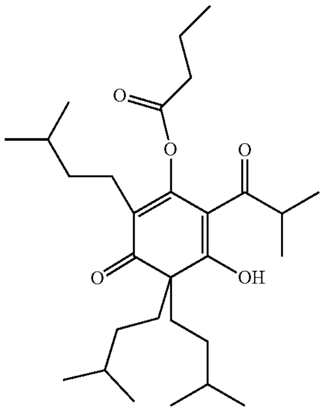
, or -continued (I2-4)

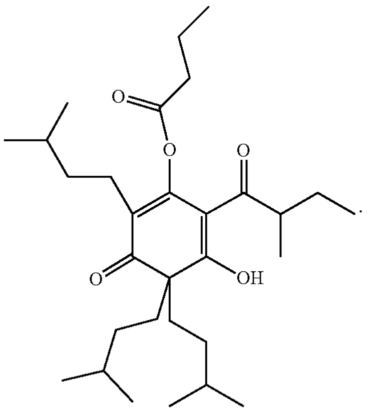

10. The feed composition according to claim 5, wherein the feed composition further comprises an additional additive and/or an animal feed ingredient.

11. The feed composition according to claim 10, wherein the additional additive is a nutritional additive, a non-nutritional additive, a medicinal feed additive, or a combination thereof.

12. A method of preparing an additive for an animal feed comprising mixing the prodrug of claim 1 with a carrier, a diluent, an additive for feed, or a combination thereof, wherein the additive for feed comprises a nutritional additive, a non-nutritional additive, a medicinal feed additive, or a combination thereof.

13. A method of preparing an animal feed comprising mixing the prodrug of claim 1 with an additive for feed, wherein the additive for feed comprises a nutritional additive, a non-nutritional additive, a medicinal feed additive, or a combination thereof.

14. A method for increasing the production performance of an animal, wherein the method comprises: feeding the animal with the feed composition of claim 5, or feeding the animal with a feed comprising the feed composition of claim 5.

15. A method of preparing an additive for an animal feed comprising mixing the feed composition of claim 5 with an additive for feed, wherein the additive for feed comprises a nutritional additive, a non-nutritional additive, a medicinal feed additive, or a combination thereof.

16. A method of preparing an animal feed comprising mixing of the feed composition claim 5 with an additive for feed, wherein the additive for feed comprises a nutritional additive, a non-nutritional additive, a medicinal feed additive, or a combination thereof.

17. A method for increasing the production performance of an animal, wherein the method comprises: feeding the animal with a hexahydro-β-acid compound having formula (I), or a solvate thereof, or a feed-acceptable salt thereof; or feeding the animal with a feed composition comprising a hexahydro-β-acid compound having formula (I), or a solvate thereof, or a feed-acceptable salt thereof:

(I)

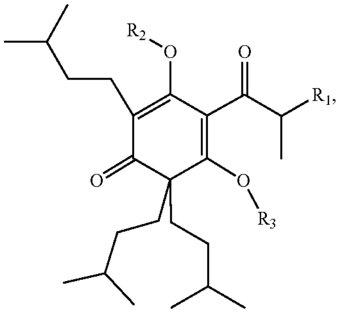

wherein $R_1$ is selected from a substituted or unsubstituted $C_1$-$C_2$ alkyl; and each of $R_2$ and $R_3$ is independently selected from H and a linear or branched $C_2$-$C_4$ carbonyl, wherein the $C_2$-$C_4$ carbonyl is substituted or unsubstituted, with the proviso that $R_2$ and $R_3$ are not both H.

18. The method according to claim 17, wherein each of the $R_2$ and $R_3$ is independently selected from H and $C(=O)CH_2CH_3$.

19. The method according to claim 17, wherein each of the $R_2$ and $R_3$ is independently selected from H and $C(=O)(CH_2)_2CH_3$.

20. The method according to claim 17, wherein the prodrug has one of the formulas below:

(I2-1)

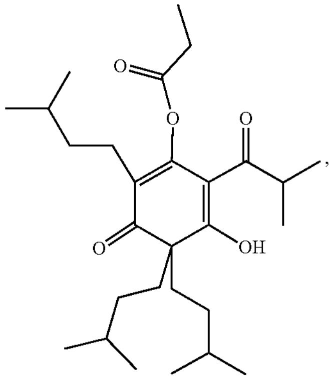

(I2-2)

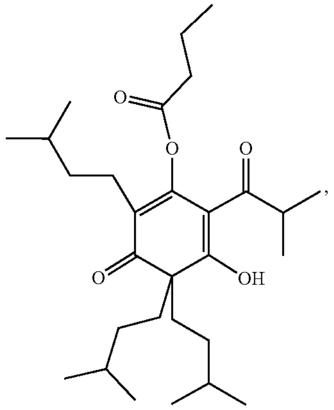

-continued
(I2-3)
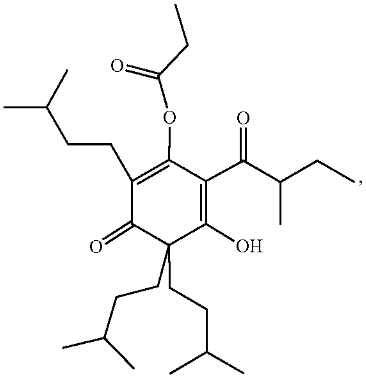
,
(I2-4)
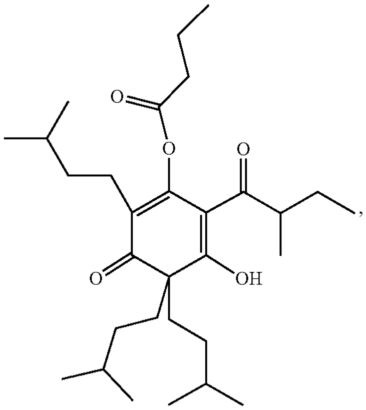
,
(I2-5)
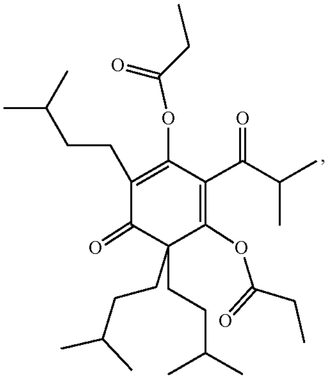
,
-continued
(I2-6)
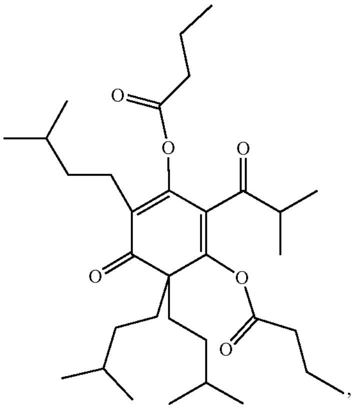
,
(I2-7)
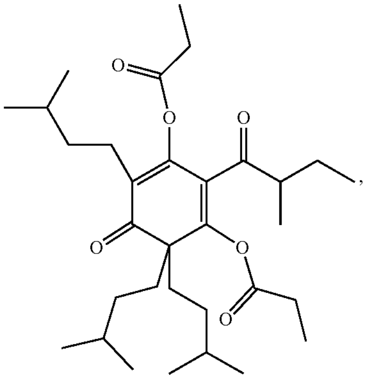
, and
(I2-8)
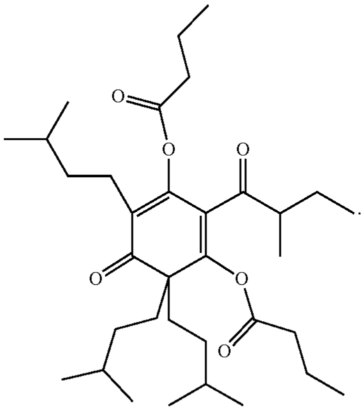
.
* * * * *